United States Patent
Feldman

(10) Patent No.: US 8,506,482 B2
(45) Date of Patent: Aug. 13, 2013

(54) METHOD AND SYSTEM FOR PROVIDING CONTINUOUS CALIBRATION OF IMPLANTABLE ANALYTE SENSORS

(75) Inventor: Benjamin J. Feldman, Oakland, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 326 days.

(21) Appl. No.: 13/022,620

(22) Filed: Feb. 7, 2011

(65) Prior Publication Data

US 2011/0130639 A1    Jun. 2, 2011

Related U.S. Application Data

(63) Continuation of application No. 11/365,340, filed on Feb. 28, 2006, now Pat. No. 7,885,698.

(51) Int. Cl.
*A61B 5/05* (2006.01)

(52) U.S. Cl.
USPC ............ 600/365; 600/309; 600/345; 600/347

(58) Field of Classification Search
USPC .................. 600/309, 345, 347, 365
See application file for complete search history.

(56) References Cited

U.S. PATENT DOCUMENTS

| | | | |
|---|---|---|---|
| 3,164,534 A | 1/1965 | Free | |
| 3,581,062 A | 5/1971 | Aston | |
| 3,926,760 A | 12/1975 | Allen et al. | |
| 3,949,388 A | 4/1976 | Fuller | |
| 4,036,749 A | 7/1977 | Anderson | |
| 4,055,175 A | 10/1977 | Clemens et al. | |
| 4,129,128 A | 12/1978 | McFarlane | |
| 4,245,634 A | 1/1981 | Albisser et al. | |
| 4,327,725 A | 5/1982 | Cortese et al. | |
| 4,344,438 A | 8/1982 | Schultz | |
| 4,349,728 A | 9/1982 | Phillips et al. | |
| 4,373,527 A | 2/1983 | Fischell | |
| 4,392,849 A | 7/1983 | Petre et al. | |
| 4,425,920 A | 1/1984 | Bourland et al. | |
| 4,431,004 A | 2/1984 | Bessman et al. | |
| 4,441,968 A | 4/1984 | Emmer et al. | |
| 4,478,976 A | 10/1984 | Goertz et al. | |
| 4,494,950 A | 1/1985 | Fischell | |
| 4,509,531 A | 4/1985 | Ward | |
| 4,527,240 A | 7/1985 | Kvitash | |

(Continued)

FOREIGN PATENT DOCUMENTS

| DE | 150656 | 9/1981 |
|---|---|---|
| DE | 4401400 | 7/1995 |

(Continued)

OTHER PUBLICATIONS

Armour, J. C., et al., "Application of Chronic Intravascular Blood Glucose Sensor in Dogs", *Diabetes*, vol. 39, 1990, pp. 1519-1526.

(Continued)

*Primary Examiner* — Patricia Mallari
*Assistant Examiner* — Christian Jang
(74) *Attorney, Agent, or Firm* — Jackson & Co., LLP

(57) ABSTRACT

Method and system for providing continuous calibration of analyte sensors includes calibrating a first sensor, receiving data associated with detected analyte levels from the first sensor, and calibrating a second sensor based on a predetermined scaling factor and data associated with detected analyte levels from the first sensor, is disclosed.

19 Claims, 7 Drawing Sheets

(56) References Cited

U.S. PATENT DOCUMENTS

| | | |
|---|---|---|
| 4,538,616 A | 9/1985 | Rogoff |
| 4,550,076 A | 10/1985 | Chikazawa et al. |
| 4,619,793 A | 10/1986 | Lee |
| 4,671,288 A | 6/1987 | Gough |
| 4,703,756 A | 11/1987 | Gough et al. |
| 4,731,726 A | 3/1988 | Allen, III |
| 4,749,985 A | 6/1988 | Corsberg |
| 4,757,022 A | 7/1988 | Shults et al. |
| 4,777,953 A | 10/1988 | Ash et al. |
| 4,779,618 A | 10/1988 | Mund et al. |
| 4,820,399 A | 4/1989 | Senda et al. |
| 4,854,322 A | 8/1989 | Ash et al. |
| 4,871,351 A | 10/1989 | Feingold |
| 4,890,620 A | 1/1990 | Gough |
| 4,891,104 A | 1/1990 | Liston et al. |
| 4,897,162 A | 1/1990 | Lewandowski et al. |
| 4,925,268 A | 5/1990 | Iyer et al. |
| 4,953,552 A | 9/1990 | DeMarzo |
| 4,974,929 A | 12/1990 | Curry |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,050,612 A | 9/1991 | Matsumura |
| 5,055,171 A | 10/1991 | Peck |
| 5,068,536 A | 11/1991 | Rosenthal |
| 5,077,476 A | 12/1991 | Rosenthal |
| 5,082,550 A | 1/1992 | Rishpon et al. |
| 5,106,365 A | 4/1992 | Hernandez |
| 5,122,925 A | 6/1992 | Inpyn |
| 5,165,407 A | 11/1992 | Wilson et al. |
| 5,200,051 A | 4/1993 | Cozzette et al. |
| 5,202,261 A | 4/1993 | Musho et al. |
| 5,202,317 A | 4/1993 | Bruice |
| 5,210,778 A | 5/1993 | Massart |
| 5,217,966 A | 6/1993 | Bruice |
| 5,227,405 A | 7/1993 | Fridovich et al. |
| 5,246,867 A | 9/1993 | Lakowicz et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,320,725 A | 6/1994 | Gregg et al. |
| 5,322,063 A | 6/1994 | Allen et al. |
| 5,340,722 A | 8/1994 | Wolfbeis et al. |
| 5,342,789 A | 8/1994 | Chick et al. |
| 5,356,786 A | 10/1994 | Heller et al. |
| 5,360,404 A | 11/1994 | Novacek et al. |
| 5,372,427 A | 12/1994 | Padovani et al. |
| 5,379,238 A | 1/1995 | Stark |
| 5,390,671 A | 2/1995 | Lord et al. |
| 5,391,250 A | 2/1995 | Cheney, II et al. |
| 5,408,999 A | 4/1995 | Singh et al. |
| 5,411,647 A | 5/1995 | Johnson et al. |
| 5,425,868 A | 6/1995 | Pedersen |
| 5,431,160 A | 7/1995 | Wilkins |
| 5,431,921 A | 7/1995 | Thombre |
| 5,462,645 A | 10/1995 | Albery et al. |
| 5,466,575 A | 11/1995 | Cozzette et al. |
| 5,468,562 A | 11/1995 | Farivar et al. |
| 5,497,772 A | 3/1996 | Schulman et al. |
| 5,507,288 A | 4/1996 | Bocker et al. |
| 5,509,410 A | 4/1996 | Hill et al. |
| 5,514,718 A | 5/1996 | Lewis et al. |
| 5,531,878 A | 7/1996 | Vadgama et al. |
| 5,552,997 A | 9/1996 | Massart |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,609,575 A | 3/1997 | Larson et al. |
| 5,610,293 A | 3/1997 | Riley et al. |
| 5,628,310 A | 5/1997 | Rao et al. |
| 5,640,954 A | 6/1997 | Pfeiffer et al. |
| 5,651,869 A | 7/1997 | Yoshioka et al. |
| 5,653,239 A | 8/1997 | Pompei et al. |
| 5,665,222 A | 9/1997 | Heller et al. |
| 5,696,109 A | 12/1997 | Malfroy-Camine et al. |
| 5,711,001 A | 1/1998 | Bussan et al. |
| 5,711,861 A | 1/1998 | Ward et al. |
| 5,733,259 A | 3/1998 | Valcke et al. |
| 5,771,890 A | 6/1998 | Tamada |
| 5,772,586 A | 6/1998 | Heinonen et al. |
| 5,791,344 A | 8/1998 | Schulman et al. |
| 5,814,020 A | 9/1998 | Gross |
| 5,820,570 A | 10/1998 | Erickson et al. |
| 5,858,001 A | 1/1999 | Tsals et al. |
| 5,882,494 A | 3/1999 | Van Antwerp |
| 5,899,855 A | 5/1999 | Brown |
| 5,906,921 A | 5/1999 | Ikeda et al. |
| 5,914,026 A | 6/1999 | Blubaugh et al. |
| 5,925,021 A | 7/1999 | Castellano et al. |
| 5,931,814 A | 8/1999 | Alex et al. |
| 5,935,224 A | 8/1999 | Svancarek et al. |
| 5,942,979 A | 8/1999 | Luppino |
| 5,947,957 A | 9/1999 | Morris |
| 5,957,854 A | 9/1999 | Besson et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,972,199 A | 10/1999 | Heller et al. |
| 5,993,411 A | 11/1999 | Choi |
| 5,994,339 A | 11/1999 | Crapo et al. |
| 5,995,860 A | 11/1999 | Sun et al. |
| 5,997,501 A | 12/1999 | Gross et al. |
| 6,001,067 A | 12/1999 | Shults et al. |
| 6,004,278 A | 12/1999 | Botich et al. |
| 6,011,077 A | 1/2000 | Muller |
| 6,023,629 A | 2/2000 | Tamada |
| 6,024,699 A | 2/2000 | Surwit et al. |
| 6,049,727 A | 4/2000 | Crothall |
| 6,081,736 A | 6/2000 | Colvin et al. |
| 6,083,710 A | 7/2000 | Heller et al. |
| 6,084,093 A | 7/2000 | Riley et al. |
| 6,088,608 A | 7/2000 | Schulman et al. |
| 6,091,976 A | 7/2000 | Pfeiffer et al. |
| 6,093,172 A | 7/2000 | Funderburk et al. |
| 6,103,033 A | 8/2000 | Say et al. |
| 6,103,714 A | 8/2000 | Fridovich et al. |
| 6,110,155 A | 8/2000 | Baudino |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,122,536 A | 9/2000 | Sun et al. |
| 6,127,356 A | 10/2000 | Crapo et al. |
| 6,134,461 A | 10/2000 | Say et al. |
| 6,143,164 A | 11/2000 | Heller et al. |
| 6,144,869 A | 11/2000 | Berner et al. |
| 6,162,611 A | 12/2000 | Heller et al. |
| 6,175,752 B1 | 1/2001 | Say et al. |
| 6,186,982 B1 | 2/2001 | Gross et al. |
| 6,190,315 B1 | 2/2001 | Kost et al. |
| 6,200,265 B1 | 3/2001 | Walsh et al. |
| 6,212,416 B1 | 4/2001 | Ward et al. |
| 6,214,817 B1 | 4/2001 | Riley et al. |
| 6,219,574 B1 | 4/2001 | Cormier et al. |
| 6,233,471 B1 | 5/2001 | Berner et al. |
| 6,245,758 B1 | 6/2001 | Stern et al. |
| 6,248,067 B1 | 6/2001 | Causey, III et al. |
| 6,254,586 B1 | 7/2001 | Mann et al. |
| 6,267,002 B1 | 7/2001 | Ehwald et al. |
| 6,268,161 B1 | 7/2001 | Han et al. |
| 6,275,717 B1 | 8/2001 | Gross et al. |
| 6,284,478 B1 | 9/2001 | Heller et al. |
| 6,293,925 B1 | 9/2001 | Safabash et al. |

| Patent | Date | Inventor |
|---|---|---|
| 6,295,506 B1 | 9/2001 | Heinonen et al. |
| 6,298,254 B2 | 10/2001 | Tamada |
| 6,299,347 B1 | 10/2001 | Pompei |
| 6,306,104 B1 | 10/2001 | Cunningham et al. |
| 6,309,884 B1 | 10/2001 | Cooper et al. |
| 6,329,161 B1 | 12/2001 | Heller et al. |
| 6,331,244 B1 | 12/2001 | Lewis et al. |
| 6,338,790 B1 | 1/2002 | Feldman et al. |
| 6,343,225 B1 | 1/2002 | Clark, Jr. |
| 6,360,888 B1 | 3/2002 | McIvor et al. |
| 6,366,794 B1 | 4/2002 | Moussy et al. |
| 6,368,141 B1 | 4/2002 | Van Antwerp et al. |
| 6,368,274 B1 | 4/2002 | Van Antwerp et al. |
| 6,372,045 B1 | 4/2002 | McCabe et al. |
| 6,377,828 B1 | 4/2002 | Chaiken et al. |
| 6,379,301 B1 | 4/2002 | Worthington et al. |
| 6,400,974 B1 | 6/2002 | Lesho |
| 6,403,788 B1 | 6/2002 | Meunier et al. |
| 6,418,332 B1 | 7/2002 | Mastrototaro et al. |
| 6,424,847 B1 | 7/2002 | Mastrototaro et al. |
| 6,427,088 B1 | 7/2002 | Bowman, IV et al. |
| 6,434,409 B1 | 8/2002 | Pfeiffer et al. |
| 6,436,255 B2 | 8/2002 | Yamamoto et al. |
| 6,438,414 B1 | 8/2002 | Conn et al. |
| 6,440,068 B1 | 8/2002 | Brown et al. |
| 6,445,374 B2 | 9/2002 | Albert et al. |
| 6,448,239 B1 | 9/2002 | Groves et al. |
| 6,466,810 B1 | 10/2002 | Ward et al. |
| 6,475,181 B1 | 11/2002 | Potter et al. |
| 6,475,196 B1 | 11/2002 | Vachon |
| 6,477,395 B2 | 11/2002 | Schulman et al. |
| 6,477,891 B2 | 11/2002 | Ehwald et al. |
| 6,478,736 B1 | 11/2002 | Mault |
| 6,479,477 B1 | 11/2002 | Crapo et al. |
| 6,482,176 B1 | 11/2002 | Wich |
| 6,484,046 B1 | 11/2002 | Say et al. |
| 6,491,657 B2 | 12/2002 | Rowe et al. |
| 6,493,069 B1 | 12/2002 | Nagashimada et al. |
| 6,497,729 B1 | 12/2002 | Moussy et al. |
| 6,508,785 B1 | 1/2003 | Eppstein |
| 6,512,939 B1 | 1/2003 | Colvin et al. |
| 6,514,718 B2 | 2/2003 | Heller et al. |
| 6,525,041 B1 | 2/2003 | Neumann et al. |
| 6,530,915 B1 | 3/2003 | Eppstein et al. |
| 6,541,490 B1 | 4/2003 | Campbell et al. |
| 6,544,212 B2 | 4/2003 | Galley et al. |
| 6,544,975 B1 | 4/2003 | Crapo et al. |
| 6,551,494 B1 | 4/2003 | Heller et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,573,257 B2 | 6/2003 | Malfroy-Camine et al. |
| 6,576,101 B1 | 6/2003 | Heller et al. |
| 6,577,899 B2 | 6/2003 | Lebel et al. |
| 6,579,690 B1 | 6/2003 | Bonnecaze et al. |
| 6,585,644 B2 | 7/2003 | Lebel et al. |
| 6,589,948 B1 | 7/2003 | Malfroy-Camine et al. |
| 6,591,125 B1 | 7/2003 | Buse et al. |
| 6,591,126 B2 | 7/2003 | Roeper et al. |
| 6,592,746 B1 | 7/2003 | Schmid-Schoenbein et al. |
| 6,595,919 B2 | 7/2003 | Berner et al. |
| 6,599,407 B2 | 7/2003 | Taniike et al. |
| 6,602,678 B2 | 8/2003 | Kwon et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,620,123 B1 | 9/2003 | Mitragotri et al. |
| 6,633,772 B2 | 10/2003 | Ford et al. |
| 6,635,014 B2 | 10/2003 | Starkweather et al. |
| 6,648,821 B2 | 11/2003 | Lebel et al. |
| 6,654,625 B1 | 11/2003 | Say et al. |
| 6,659,948 B2 | 12/2003 | Lebel et al. |
| 6,668,196 B1 | 12/2003 | Villegas et al. |
| 6,676,816 B2 | 1/2004 | Mao et al. |
| 6,679,841 B2 | 1/2004 | Bojan et al. |
| 6,685,699 B1 | 2/2004 | Eppstein et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Baber et al. |
| 6,702,857 B2 | 3/2004 | Brauker et al. |
| 6,723,077 B2 | 4/2004 | Pickup et al. |
| 6,733,446 B2 | 5/2004 | Lebel et al. |
| 6,740,075 B2 | 5/2004 | Lebel et al. |
| 6,740,215 B1 | 5/2004 | Nakaminami et al. |
| 6,741,877 B1 | 5/2004 | Shults et al. |
| 6,746,582 B2 | 6/2004 | Heller et al. |
| 6,758,810 B2 | 7/2004 | Lebel et al. |
| 6,770,030 B1 | 8/2004 | Schaupp et al. |
| 6,770,729 B2 | 8/2004 | Van Antwerp |
| 6,790,178 B1 | 9/2004 | Mault et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,835,387 B2 | 12/2004 | Herrmann |
| 6,837,988 B2 | 1/2005 | Leong et al. |
| 6,862,465 B2 | 3/2005 | Shults et al. |
| 6,865,407 B2 | 3/2005 | Kimball et al. |
| 6,873,268 B2 | 3/2005 | Lebel et al. |
| 6,881,551 B2 | 4/2005 | Heller et al. |
| 6,885,196 B2 | 4/2005 | Taniike et al. |
| 6,892,085 B2 | 5/2005 | McIvor et al. |
| 6,895,263 B2 | 5/2005 | Shin et al. |
| 6,895,265 B2 | 5/2005 | Silver |
| 6,931,327 B2 | 8/2005 | Goode, Jr. et al. |
| 6,932,894 B2 | 8/2005 | Mao et al. |
| 6,936,006 B2 | 8/2005 | Sabra |
| 6,950,708 B2 | 9/2005 | Bowman, IV et al. |
| 6,958,705 B2 | 10/2005 | Lebel et al. |
| 6,968,294 B2 | 11/2005 | Gutta et al. |
| 6,971,274 B2 | 12/2005 | Olin |
| 6,971,999 B2 | 12/2005 | Py et al. |
| 6,974,437 B2 | 12/2005 | Lebel et al. |
| 6,990,366 B2 | 1/2006 | Say et al. |
| 6,997,907 B2 | 2/2006 | Safabash et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,022,072 B2 | 4/2006 | Fox et al. |
| 7,024,245 B2 | 4/2006 | Lebel et al. |
| 7,027,931 B1 | 4/2006 | Jones et al. |
| 7,029,444 B2 | 4/2006 | Shin et al. |
| 7,041,068 B2 | 5/2006 | Freeman et al. |
| 7,052,483 B2 | 5/2006 | Wojcik |
| 7,056,302 B2 | 6/2006 | Douglas |
| 7,074,307 B2 | 7/2006 | Simpson et al. |
| 7,081,195 B2 | 7/2006 | Simpson et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,134,999 B2 | 11/2006 | Brauker et al. |
| 7,136,689 B2 | 11/2006 | Shults et al. |
| 7,153,265 B2 | 12/2006 | Vachon |
| 7,171,274 B2 | 1/2007 | Starkweather et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,225,535 B2 | 6/2007 | Feldman et al. |
| 7,226,978 B2 | 6/2007 | Tapsak et al. |
| 7,258,673 B2 | 8/2007 | Racchini et al. |
| 7,267,665 B2 | 9/2007 | Steil et al. |
| 7,276,029 B2 | 10/2007 | Goode et al. |
| 7,295,867 B2 | 11/2007 | Berner et al. |
| 7,299,082 B2 | 11/2007 | Feldman et al. |

| | | | | | | |
|---|---|---|---|---|---|---|
| 7,310,544 B2 | 12/2007 | Brister et al. | | 2003/0118577 A1 | 6/2003 | Weill et al. |
| 7,335,294 B2 | 2/2008 | Heller et al. | | 2003/0125612 A1 | 7/2003 | Fox et al. |
| 7,354,420 B2 | 4/2008 | Steil et al. | | 2003/0130616 A1 | 7/2003 | Steil et al. |
| 7,364,592 B2 | 4/2008 | Carr-Brendel et al. | | 2003/0134347 A1 | 7/2003 | Heller et al. |
| 7,366,556 B2 | 4/2008 | Brister et al. | | 2003/0168338 A1 | 9/2003 | Gao et al. |
| 7,379,765 B2 | 5/2008 | Petisce et al. | | 2003/0176933 A1 | 9/2003 | Lebel et al. |
| 7,402,153 B2 | 7/2008 | Steil et al. | | 2003/0187338 A1 | 10/2003 | Say et al. |
| 7,424,318 B2 | 9/2008 | Brister et al. | | 2003/0190341 A1 | 10/2003 | Shalaby et al. |
| 7,460,898 B2 | 12/2008 | Brister et al. | | 2003/0191377 A1 | 10/2003 | Robinson et al. |
| 7,467,003 B2 | 12/2008 | Brister et al. | | 2003/0199790 A1 | 10/2003 | Boecker et al. |
| 7,471,972 B2 | 12/2008 | Rhodes et al. | | 2003/0199837 A1 | 10/2003 | Vachon |
| 7,494,465 B2 | 2/2009 | Brister et al. | | 2003/0208113 A1 | 11/2003 | Mault et al. |
| 7,497,827 B2 | 3/2009 | Brister et al. | | 2003/0212317 A1 | 11/2003 | Kovatchev et al. |
| 7,519,408 B2 | 4/2009 | Rasdal et al. | | 2003/0212346 A1 | 11/2003 | Yuzhakov et al. |
| 7,547,281 B2 | 6/2009 | Hayes et al. | | 2003/0212379 A1 | 11/2003 | Bylund et al. |
| 7,569,030 B2 | 8/2009 | Lebel et al. | | 2003/0216630 A1 | 11/2003 | Jersey-Willuhn et al. |
| 7,583,990 B2 | 9/2009 | Goode et al. | | 2003/0217966 A1 | 11/2003 | Tapsak et al. |
| 7,591,801 B2 | 9/2009 | Brauker et al. | | 2004/0010186 A1 | 1/2004 | Kimball et al. |
| 7,599,726 B2 | 10/2009 | Goode et al. | | 2004/0010207 A1 | 1/2004 | Flaherty et al. |
| 7,613,491 B2 | 11/2009 | Boock et al. | | 2004/0011671 A1 | 1/2004 | Shults et al. |
| 7,615,007 B2 | 11/2009 | Shults et al. | | 2004/0024553 A1 | 2/2004 | Monfre et al. |
| 7,618,369 B2 | 11/2009 | Hayter et al. | | 2004/0028612 A1 | 2/2004 | Singaram et al. |
| 7,632,228 B2 | 12/2009 | Brauker et al. | | 2004/0039298 A1 | 2/2004 | Abreu |
| 7,637,868 B2 | 12/2009 | Saint et al. | | 2004/0040840 A1 | 3/2004 | Mao et al. |
| 7,640,048 B2 | 12/2009 | Dobbles et al. | | 2004/0045879 A1 | 3/2004 | Shults et al. |
| 7,651,596 B2 | 1/2010 | Petisce et al. | | 2004/0063167 A1 | 4/2004 | Kaastrup et al. |
| 7,653,425 B2 | 1/2010 | Hayter et al. | | 2004/0064068 A1 | 4/2004 | DeNuzzio et al. |
| 7,654,956 B2 | 2/2010 | Brister et al. | | 2004/0064133 A1 | 4/2004 | Miller et al. |
| 7,657,297 B2 | 2/2010 | Simpson et al. | | 2004/0074785 A1 | 4/2004 | Holker et al. |
| 7,697,967 B2 | 4/2010 | Stafford | | 2004/0099529 A1 | 5/2004 | Mao et al. |
| 7,699,694 B2 | 4/2010 | Feldman et al. | | 2004/0106858 A1 | 6/2004 | Say et al. |
| 7,711,402 B2 | 5/2010 | Shults et al. | | 2004/0110722 A1 | 6/2004 | Ornberg et al. |
| 7,713,574 B2 | 5/2010 | Brister et al. | | 2004/0116332 A1 | 6/2004 | Ornberg et al. |
| 7,715,893 B2 | 5/2010 | Kamath et al. | | 2004/0116847 A1 | 6/2004 | Wall |
| 7,774,145 B2 | 8/2010 | Brauker et al. | | 2004/0122353 A1 | 6/2004 | Shahmirian et al. |
| 7,778,680 B2 | 8/2010 | Goode, Jr. et al. | | 2004/0133164 A1 | 7/2004 | Funderburk et al. |
| 7,778,795 B2 | 8/2010 | Fukushima et al. | | 2004/0138588 A1 | 7/2004 | Saikley et al. |
| 7,826,981 B2 | 11/2010 | Goode, Jr. et al. | | 2004/0146909 A1 | 7/2004 | Duong et al. |
| 7,882,611 B2 | 2/2011 | Shah et al. | | 2004/0152622 A1 | 8/2004 | Keith et al. |
| 7,905,833 B2 | 3/2011 | Brister et al. | | 2004/0167801 A1 | 8/2004 | Say et al. |
| 7,911,010 B2 | 3/2011 | Stetter | | 2004/0171921 A1 | 9/2004 | Say et al. |
| 7,914,450 B2 | 3/2011 | Goode, Jr. et al. | | 2004/0176672 A1 | 9/2004 | Silver et al. |
| 7,954,385 B2 | 6/2011 | Raisanen | | 2004/0186362 A1 | 9/2004 | Brauker et al. |
| 7,974,672 B2 | 7/2011 | Shults et al. | | 2004/0186365 A1 | 9/2004 | Jin et al. |
| 2001/0020125 A1 | 9/2001 | Kurnik et al. | | 2004/0193025 A1 | 9/2004 | Steil et al. |
| 2001/0039393 A1 | 11/2001 | Mori et al. | | 2004/0193090 A1 | 9/2004 | Lebel et al. |
| 2001/0041830 A1 | 11/2001 | Varalli et al. | | 2004/0197846 A1 | 10/2004 | Hockersmith et al. |
| 2002/0006634 A1 | 1/2002 | Han et al. | | 2004/0199059 A1 | 10/2004 | Brauker et al. |
| 2002/0019022 A1 | 2/2002 | Dunn et al. | | 2004/0204687 A1 | 10/2004 | Mogensen et al. |
| 2002/0023852 A1 | 2/2002 | McIvor et al. | | 2004/0204868 A1 | 10/2004 | Maynard et al. |
| 2002/0026110 A1 | 2/2002 | Parris et al. | | 2004/0225338 A1 | 11/2004 | Lebel et al. |
| 2002/0042090 A1 | 4/2002 | Heller et al. | | 2004/0236200 A1 | 11/2004 | Say et al. |
| 2002/0042407 A1 | 4/2002 | Fridovich et al. | | 2004/0254434 A1 | 12/2004 | Goodnow et al. |
| 2002/0055711 A1 | 5/2002 | Lavi et al. | | 2004/0263354 A1 | 12/2004 | Mann et al. |
| 2002/0068860 A1 | 6/2002 | Clark | | 2004/0267300 A1 | 12/2004 | Mace |
| 2002/0082490 A1 | 6/2002 | Roeper et al. | | 2005/0004439 A1 | 1/2005 | Shin et al. |
| 2002/0082543 A1 | 6/2002 | Park et al. | | 2005/0004494 A1 | 1/2005 | Perez et al. |
| 2002/0103499 A1 | 8/2002 | Perez et al. | | 2005/0010269 A1 | 1/2005 | Lebel et al. |
| 2002/0106709 A1 | 8/2002 | Potts et al. | | 2005/0027177 A1 | 2/2005 | Shin et al. |
| 2002/0128594 A1 | 9/2002 | Das et al. | | 2005/0027180 A1 | 2/2005 | Goode et al. |
| 2002/0161288 A1 | 10/2002 | Shin et al. | | 2005/0027181 A1 | 2/2005 | Goode et al. |
| 2002/0169635 A1 | 11/2002 | Shillingburg | | 2005/0027462 A1 | 2/2005 | Goode et al. |
| 2002/0183604 A1 | 12/2002 | Gowda et al. | | 2005/0027463 A1 | 2/2005 | Goode et al. |
| 2003/0004403 A1 | 1/2003 | Drinan et al. | | 2005/0031689 A1 | 2/2005 | Shults et al. |
| 2003/0023317 A1 | 1/2003 | Brauker et al. | | 2005/0033132 A1 | 2/2005 | Shults et al. |
| 2003/0031699 A1 | 2/2003 | Van Antwerp | | 2005/0038332 A1 | 2/2005 | Saidara et al. |
| 2003/0032874 A1 | 2/2003 | Rhodes et al. | | 2005/0043598 A1 | 2/2005 | Goode, Jr. et al. |
| 2003/0042137 A1 | 3/2003 | Mao et al. | | 2005/0054909 A1 | 3/2005 | Petisce et al. |
| 2003/0045798 A1 | 3/2003 | Hular et al. | | 2005/0090607 A1 | 4/2005 | Tapsak et al. |
| 2003/0055032 A1 | 3/2003 | Groves et al. | | 2005/0096511 A1 | 5/2005 | Fox et al. |
| 2003/0060692 A1 | 3/2003 | Ruchti et al. | | 2005/0096512 A1 | 5/2005 | Fox et al. |
| 2003/0065254 A1 | 4/2003 | Schulman et al. | | 2005/0096520 A1 | 5/2005 | Maekawa et al. |
| 2003/0065308 A1 | 4/2003 | Lebel et al. | | 2005/0112169 A1 | 5/2005 | Brauker et al. |
| 2003/0069281 A1 | 4/2003 | Fridovich et al. | | 2005/0113653 A1 | 5/2005 | Fox et al. |
| 2003/0077702 A1 | 4/2003 | Shah et al. | | 2005/0114068 A1 | 5/2005 | Chey et al. |
| 2003/0077772 A1 | 4/2003 | Shah et al. | | 2005/0121322 A1 | 6/2005 | Say et al. |
| 2003/0078560 A1 | 4/2003 | Miller et al. | | 2005/0131346 A1 | 6/2005 | Douglas |
| 2003/0099682 A1 | 5/2003 | Moussy et al. | | 2005/0143635 A1 | 6/2005 | Kamath et al. |
| 2003/0100821 A1 | 5/2003 | Heller et al. | | 2005/0173245 A1 | 8/2005 | Feldman et al. |

| | | | | | | |
|---|---|---|---|---|---|---|
| 2005/0176136 A1 | 8/2005 | Burd et al. | | 2007/0191701 A1 | 8/2007 | Feldman et al. |
| 2005/0177398 A1 | 8/2005 | Watanabe et al. | | 2007/0203407 A1 | 8/2007 | Hoss et al. |
| 2005/0182306 A1 | 8/2005 | Sloan | | 2007/0203966 A1 | 8/2007 | Brauker et al. |
| 2005/0187720 A1 | 8/2005 | Goode, Jr. et al. | | 2007/0219496 A1 | 9/2007 | Kamen et al. |
| 2005/0192557 A1 | 9/2005 | Brauker et al. | | 2007/0235331 A1 | 10/2007 | Simpson et al. |
| 2005/0195930 A1 | 9/2005 | Spital et al. | | 2007/0249922 A1 | 10/2007 | Peyser et al. |
| 2005/0199494 A1 | 9/2005 | Say et al. | | 2007/0258395 A1 | 11/2007 | Jollota et al. |
| 2005/0203360 A1 | 9/2005 | Brauker et al. | | 2008/0009692 A1 | 1/2008 | Stafford |
| 2005/0215871 A1 | 9/2005 | Feldman et al. | | 2008/0017522 A1 | 1/2008 | Heller et al. |
| 2005/0239154 A1 | 10/2005 | Feldman et al. | | 2008/0021666 A1 | 1/2008 | Goode, Jr. et al. |
| 2005/0241957 A1 | 11/2005 | Mao et al. | | 2008/0029391 A1 | 2/2008 | Mao et al. |
| 2005/0245795 A1 | 11/2005 | Goode, Jr. et al. | | 2008/0030369 A1 | 2/2008 | Mann et al. |
| 2005/0245799 A1 | 11/2005 | Brauker et al. | | 2008/0033254 A1 | 2/2008 | Kamath et al. |
| 2005/0245839 A1 | 11/2005 | Stivoric et al. | | 2008/0033268 A1 | 2/2008 | Stafford |
| 2005/0245904 A1 | 11/2005 | Estes et al. | | 2008/0039702 A1 | 2/2008 | Hayter et al. |
| 2005/0287620 A1 | 12/2005 | Heller et al. | | 2008/0045824 A1 | 2/2008 | Tapsak et al. |
| 2006/0001538 A1 | 1/2006 | Kraft et al. | | 2008/0058625 A1 | 3/2008 | McGarraugh et al. |
| 2006/0004270 A1 | 1/2006 | Bedard et al. | | 2008/0064937 A1 | 3/2008 | McGarraugh et al. |
| 2006/0010098 A1 | 1/2006 | Goodnow et al. | | 2008/0071156 A1 | 3/2008 | Brister et al. |
| 2006/0015020 A1 | 1/2006 | Neale et al. | | 2008/0071157 A1 | 3/2008 | McGarraugh et al. |
| 2006/0015024 A1 | 1/2006 | Brister et al. | | 2008/0071158 A1 | 3/2008 | McGarraugh et al. |
| 2006/0016700 A1 | 1/2006 | Brister et al. | | 2008/0081977 A1 | 4/2008 | Hayter et al. |
| 2006/0017923 A1 | 1/2006 | Ruchti et al. | | 2008/0083617 A1 | 4/2008 | Simpson et al. |
| 2006/0019327 A1 | 1/2006 | Brister et al. | | 2008/0086042 A1 | 4/2008 | Brister et al. |
| 2006/0020186 A1 | 1/2006 | Brister et al. | | 2008/0086044 A1 | 4/2008 | Brister et al. |
| 2006/0020187 A1 | 1/2006 | Brister et al. | | 2008/0086273 A1 | 4/2008 | Shults et al. |
| 2006/0020188 A1 | 1/2006 | Kamath et al. | | 2008/0097246 A1 | 4/2008 | Stafford |
| 2006/0020189 A1 | 1/2006 | Brister et al. | | 2008/0097289 A1 | 4/2008 | Steil et al. |
| 2006/0020190 A1 | 1/2006 | Kamath et al. | | 2008/0108942 A1 | 5/2008 | Brister et al. |
| 2006/0020191 A1 | 1/2006 | Brister et al. | | 2008/0114280 A1 | 5/2008 | Stafford |
| 2006/0020192 A1 | 1/2006 | Brister et al. | | 2008/0119703 A1 | 5/2008 | Brister et al. |
| 2006/0029177 A1 | 2/2006 | Cranford, Jr. et al. | | 2008/0119707 A1 | 5/2008 | Stafford |
| 2006/0031094 A1 | 2/2006 | Cohen et al. | | 2008/0154513 A1 | 6/2008 | Kovatchev et al. |
| 2006/0036139 A1 | 2/2006 | Brister et al. | | 2008/0167543 A1 | 7/2008 | Say et al. |
| 2006/0036140 A1 | 2/2006 | Brister et al. | | 2008/0172205 A1 | 7/2008 | Breton et al. |
| 2006/0036141 A1 | 2/2006 | Kamath et al. | | 2008/0183060 A1 | 7/2008 | Steil et al. |
| 2006/0036142 A1 | 2/2006 | Brister et al. | | 2008/0183061 A1 | 7/2008 | Goode et al. |
| 2006/0036143 A1 | 2/2006 | Brister et al. | | 2008/0183399 A1 | 7/2008 | Goode et al. |
| 2006/0036144 A1 | 2/2006 | Brister et al. | | 2008/0188731 A1 | 8/2008 | Brister et al. |
| 2006/0036145 A1 | 2/2006 | Brister | | 2008/0188796 A1 | 8/2008 | Steil et al. |
| 2006/0155180 A1 | 7/2006 | Brister et al. | | 2008/0189051 A1 | 8/2008 | Goode et al. |
| 2006/0166629 A1 | 7/2006 | Reggiardo | | 2008/0194935 A1 | 8/2008 | Brister et al. |
| 2006/0173260 A1 | 8/2006 | Gaoni et al. | | 2008/0194936 A1 | 8/2008 | Goode et al. |
| 2006/0173406 A1 | 8/2006 | Hayes et al. | | 2008/0194937 A1 | 8/2008 | Goode et al. |
| 2006/0173444 A1 | 8/2006 | Choy et al. | | 2008/0194938 A1 | 8/2008 | Brister et al. |
| 2006/0183985 A1 | 8/2006 | Brister et al. | | 2008/0195049 A1 | 8/2008 | Thalmann et al. |
| 2006/0189863 A1 | 8/2006 | Peyser et al. | | 2008/0195232 A1 | 8/2008 | Carr-Brendel et al. |
| 2006/0219576 A1 | 10/2006 | Jina et al. | | 2008/0195967 A1 | 8/2008 | Goode et al. |
| 2006/0222566 A1 | 10/2006 | Brauker et al. | | 2008/0197024 A1 | 8/2008 | Simpson et al. |
| 2006/0224109 A1 | 10/2006 | Steil et al. | | 2008/0200788 A1 | 8/2008 | Brister et al. |
| 2006/0226985 A1 | 10/2006 | Goodnow et al. | | 2008/0200789 A1 | 8/2008 | Brister et al. |
| 2006/0229512 A1 | 10/2006 | Petisce et al. | | 2008/0200791 A1 | 8/2008 | Simpson et al. |
| 2006/0247508 A1 | 11/2006 | Fennell | | 2008/0200897 A1 | 8/2008 | Hoss et al. |
| 2006/0258929 A1 | 11/2006 | Goode et al. | | 2008/0208025 A1 | 8/2008 | Shults et al. |
| 2006/0272652 A1 | 12/2006 | Stocker et al. | | 2008/0208113 A1 | 8/2008 | Damiano et al. |
| 2006/0281985 A1 | 12/2006 | Ward et al. | | 2008/0214915 A1 | 9/2008 | Brister et al. |
| 2007/0016381 A1 | 1/2007 | Kamath et al. | | 2008/0214918 A1 | 9/2008 | Brister et al. |
| 2007/0027381 A1 | 2/2007 | Stafford | | 2008/0228051 A1 | 9/2008 | Shults et al. |
| 2007/0032717 A1 | 2/2007 | Brister et al. | | 2008/0228054 A1 | 9/2008 | Shults et al. |
| 2007/0033074 A1 | 2/2007 | Nitzan et al. | | 2008/0242961 A1 | 10/2008 | Brister et al. |
| 2007/0060803 A1 | 3/2007 | Liljeryd et al. | | 2008/0255434 A1 | 10/2008 | Hayter et al. |
| 2007/0060814 A1 | 3/2007 | Stafford | | 2008/0255437 A1 | 10/2008 | Hayter |
| 2007/0066873 A1 | 3/2007 | Kamath et al. | | 2008/0255808 A1 | 10/2008 | Hayter |
| 2007/0071681 A1 | 3/2007 | Gadkar et al. | | 2008/0256048 A1 | 10/2008 | Hayter |
| 2007/0073129 A1 | 3/2007 | Shah et al. | | 2008/0262469 A1 | 10/2008 | Brister et al. |
| 2007/0078320 A1 | 4/2007 | Stafford | | 2008/0275313 A1 | 11/2008 | Brister et al. |
| 2007/0078321 A1 | 4/2007 | Mazza et al. | | 2008/0287761 A1 | 11/2008 | Hayter |
| 2007/0078322 A1 | 4/2007 | Stafford | | 2008/0287762 A1 | 11/2008 | Hayter |
| 2007/0078323 A1 | 4/2007 | Reggiardo et al. | | 2008/0287763 A1 | 11/2008 | Hayter |
| 2007/0106135 A1 | 5/2007 | Sloan et al. | | 2008/0287764 A1 | 11/2008 | Rasdal et al. |
| 2007/0124002 A1 | 5/2007 | Estes et al. | | 2008/0287765 A1 | 11/2008 | Rasdal et al. |
| 2007/0149875 A1 | 6/2007 | Ouyang et al. | | 2008/0287766 A1 | 11/2008 | Rasdal et al. |
| 2007/0163880 A1 | 7/2007 | Woo et al. | | 2008/0288180 A1 | 11/2008 | Hayter et al. |
| 2007/0163894 A1 | 7/2007 | Wang et al. | | 2008/0288204 A1 | 11/2008 | Hayter |
| 2007/0168224 A1 | 7/2007 | Letzt et al. | | 2008/0296155 A1 | 12/2008 | Shults et al. |
| 2007/0173706 A1 | 7/2007 | Neinast et al. | | 2008/0300476 A1 | 12/2008 | Stafford |
| 2007/0173761 A1 | 7/2007 | Kanderian et al. | | 2008/0306368 A1 | 12/2008 | Goode et al. |
| 2007/0179349 A1 | 8/2007 | Hoyme et al. | | 2008/0306434 A1 | 12/2008 | Dobbles et al. |
| 2007/0179352 A1 | 8/2007 | Randlov et al. | | 2008/0306435 A1 | 12/2008 | Kamath et al. |

| | | |
|---|---|---|
| 2008/0306444 A1 | 12/2008 | Brister et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2008/0314395 A1 | 12/2008 | Kovatchev et al. |
| 2009/0005665 A1 | 1/2009 | Hayter et al. |
| 2009/0006034 A1 | 1/2009 | Hayter et al. |
| 2009/0012379 A1 | 1/2009 | Goode et al. |
| 2009/0018424 A1 | 1/2009 | Kamath et al. |
| 2009/0018425 A1 | 1/2009 | Ouyang et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0062767 A1 | 3/2009 | VanAntwerp et al. |
| 2009/0063402 A1 | 3/2009 | Hayter |
| 2009/0069750 A1 | 3/2009 | Schraga |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085768 A1 | 4/2009 | Patel et al. |
| 2009/0099436 A1 | 4/2009 | Brister et al. |
| 2009/0105636 A1 | 4/2009 | Hayter et al. |
| 2009/0112478 A1 | 4/2009 | Mueller, Jr. et al. |
| 2009/0124877 A1 | 5/2009 | Goode et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0171182 A1 | 7/2009 | Stafford |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0287073 A1 | 11/2009 | Boock et al. |
| 2009/0287074 A1 | 11/2009 | Shults et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063373 A1 | 3/2010 | Kamath et al. |
| 2010/0076283 A1 | 3/2010 | Simpson et al. |
| 2010/0081906 A1 | 4/2010 | Hayter et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0119693 A1 | 5/2010 | Tapsak et al. |
| 2010/0121169 A1 | 5/2010 | Petisce et al. |
| 2010/0168546 A1 | 7/2010 | Kamath et al. |
| 2010/0277119 A1 | 11/2010 | Montague et al. |
| 2010/0324853 A1 | 12/2010 | Wang et al. |
| 2011/0160553 A1 | 6/2011 | Talbot et al. |
| 2012/0123690 A1 | 5/2012 | Wang et al. |
| 2012/0179015 A1 | 7/2012 | Mann et al. |

FOREIGN PATENT DOCUMENTS

| | | |
|---|---|---|
| EP | 0098592 | 1/1984 |
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 1048264 | 11/2000 |
| EP | 1153571 | 11/2001 |
| EP | 1568309 | 8/2005 |
| EP | 1746928 | 1/2012 |
| WO | WO-94/10560 | 5/1994 |
| WO | WO-95/31197 | 11/1995 |
| WO | WO-96/25089 | 8/1996 |
| WO | WO-96/35370 | 11/1996 |
| WO | WO-98/17199 | 4/1998 |
| WO | WO-98/35053 | 8/1998 |
| WO | WO-98/43637 | 10/1998 |
| WO | WO-99/47471 | 9/1999 |
| WO | WO-99/56613 | 11/1999 |
| WO | WO-00/49940 | 8/2000 |
| WO | WO-00/59370 | 10/2000 |
| WO | WO-00/74753 | 12/2000 |
| WO | WO-00/75144 | 12/2000 |
| WO | WO-00/78293 | 12/2000 |
| WO | WO-00/78992 | 12/2000 |
| WO | WO-01/36660 | 5/2001 |
| WO | WO-01/52935 | 7/2001 |
| WO | WO-01/54753 | 8/2001 |
| WO | WO-02/16905 | 2/2002 |
| WO | WO-02/39086 | 5/2002 |
| WO | WO-02/44187 | 6/2002 |
| WO | WO-02/058537 | 8/2002 |
| WO | WO-03/006091 | 1/2003 |

| | | |
|---|---|---|
| WO | WO-03/090509 | 4/2003 |
| WO | WO-03/053503 | 7/2003 |
| WO | WO-03/063925 | 8/2003 |
| WO | WO-03/071930 | 9/2003 |
| WO | WO-03/076893 | 9/2003 |
| WO | WO-03/082091 | 10/2003 |
| WO | WO-03/085372 | 10/2003 |
| WO | WO-03/103763 | 12/2003 |
| WO | WO-2004/007756 | 1/2004 |
| WO | WO-2004/028337 | 4/2004 |
| WO | WO-2004/061420 | 7/2004 |
| WO | WO-2005/041766 | 5/2005 |
| WO | WO-2005/078424 | 8/2005 |
| WO | WO-2005/089103 | 9/2005 |
| WO | WO-2006/024671 | 3/2006 |
| WO | WO-2006/079114 | 7/2006 |
| WO | WO-2006/118947 | 11/2006 |
| WO | WO-2007/007459 | 1/2007 |
| WO | WO-2007/016399 | 2/2007 |
| WO | WO-2007/027788 | 3/2007 |
| WO | WO-2007/041069 | 4/2007 |
| WO | WO-2007/041070 | 4/2007 |
| WO | WO-2007/041248 | 4/2007 |
| WO | WO-2007/056638 | 5/2007 |
| WO | WO-2007/101223 | 9/2007 |
| WO | WO-2007/120363 | 10/2007 |
| WO | WO-2007/126444 | 11/2007 |
| WO | WO-2007/053832 | 12/2007 |
| WO | WO-2007/143225 | 12/2007 |
| WO | WO-2008/021913 | 2/2008 |
| WO | WO-2008/042760 | 4/2008 |
| WO | WO-2008/086541 | 7/2008 |
| WO | WO-2008/043637 | 10/2008 |
| WO | WO-2008/128210 | 10/2008 |
| WO | WO-2008/130896 | 10/2008 |
| WO | WO-2008/130897 | 10/2008 |
| WO | WO-2008/130898 | 10/2008 |
| WO | WO-2008/143943 | 11/2008 |
| WO | WO-2009/018058 | 2/2009 |
| WO | WO-2009/086216 | 7/2009 |
| WO | WO-2009/096992 | 8/2009 |
| WO | WO-2009/097594 | 8/2009 |
| WO | WO-2010/077329 | 7/2012 |

OTHER PUBLICATIONS

Bennion, N., et al., "Alternate Site Glucose Testing: A Crossover Design", Diabetes Technology & Therapeutics, vol. 4, No. 1, 2002, pp. 25-33.

Blank, T. B., et al., "Clinical Results From a Non-Invasive Blood Glucose Monitor", Optical Diagnostics and Sensing of Biological Fluids and Glucose and Cholesterol Monitoring II, Proceedings of SPIE, vol. 4624, 2002, pp. 1-10.

Brooks, S. L., et al., "Development of an On-Line Glucose Sensor for Fermentation Monitoring", Biosensors, vol. 3, 1987/88, pp. 45-56.

Cass, A. E., et al., "Ferrocene-Medicated Enzyme Electrode for Amperometric Determination of Glucose", Analytical Chemistry, vol. 56, No. 4, 1984, 667-671.

Csoregi, E., et al., "Design and Optimization of a Selective Subcutaneously Implantable Glucose Electrode Based on 'Wired' Glucose Oxidase", Analytical Chemistry, vol. 67, No. 7, 1995, pp. 1240-1244.

Csoregi, E., et al., "Design, Characterization, and One-Point in Vivo Calibration of a Subcutaneously Implanted Glucose Electrode", Analytical Chemistry, vol. 66 No. 19, 1994, pp. 3131-3138.

Direcnet Study Group, "Accuracy of the GlucoWatch G2 Biographer and the Continuous Glucose Monitoring System During Hyoglycemia," Diabetes Care, vol. 27, No. 3, 2004, pp. 722-726.

Feldman, B., et al., "A Continuous Glucose Sensor Based on Wired EnzymeTM Technology—Results from a 3-Day Trial in Patients with Type 1 Diabetes", Diabetes Technology & Therapeutics, vol. 5, No. 5, 2003, pp. 769-779.

Feldman, B., et al., "Correlation of Glucose Concentrations in Interstitial Fluid and Venous Blood During Periods of Rapid Glucose Change", Abbott Diabetes Care, Inc. Freestyle Navigator Continuous Glucose Monitor Pamphlet.

Heller, A., et al., "Amperometric Biosensors Based on Three-Dimensional Hydrogel-Forming Epoxy Networks", Sensors and Actuators B, vol. 13-14, 1993, pp. 180-183.

Isermann, R., "Supervision, Fault-Detection and Fault-Diagnosis Methods—An Introduction", Control Engineering Practice, vol. 5, No. 5, 1997, pp. 639-652.

Isermann, R., et al., "Trends in the Application of Model-Based Fault Detection and Diagnosis of Technical Processes", Control Engineering Practice, vol. 5, No. 5, 1997, pp. 709-719.

Johnson, P. C., "Peripheral Circulation", John Wiley & Sons, 1978, pp. 198.

Jungheim, K., et al., "How Rapid Does Glucose Concentration Change in Daily Life of Patients with Type 1 Diabetes?", pp. 250.

Jungheim, K., et al., "Risky Delay of Hypoglycemia Detection by Glucose Monitoring at the Arm", Diabetes Care, vol. 24, No. 7, 2001, pp. 1303-1304.

Kaplan, S. M., "Wiley Electrical and Electronics Engineering Dictionary", IEEE Press, 2004, pp. 141, 142, 548, 549.

Lortz, J., et al., "What is Bluetooth? We Explain the Newest Short-Range Connectivity Technology", Smart Computing Learning Series, Wireless Computing, vol. 8, Issue 5, 2002, pp. 72-74

Maidan, R., et al., "Elimination of Electrooxidizable Interferant-Produced Currents in Amperometric Biosensors", Analytical Chemistry, vol. 64, No. 23, 1992, pp. 2889-2896.

Malin, S. F., et al., "Noninvasive Prediction of Glucose by Near-Infrared Diffuse Reflectance Spectroscopy", Clinical Chemistry, vol. 45, No. 9, 1999, pp. 1651-1658.

Mauras, N., et al., "Lack of Accuracy of Continuous Glucose Sensors in Healthy, Nondiabetic Children: Results of the Diabetes Research in Children Network (DirecNet) Accuracy Study," Journal of Pediatrics, 2004, pp. 770-775.

McGarraugh, G., et al., "Glucose Measurements Using Blood Extracted from the Forearm and the Finger", TheraSense, Inc., 16 Pages.

McGarraugh, G., et al., "Physiological Influences on Off-Finger Glucose Testing", Diabetes Technology & Therapeutics, vol. 3, No. 3, 2001, pp. 367-376.

McKean, B. D., et al., "A Telemetry-Instrumentation System for Chronically Implanted Glucose and Oxygen Sensors", IEEE Transactions on Biomedical Engineering, vol. 35, No. 7, 1988, pp. 526-532.

Metzger, M., et al., "Reproducibility of Glucose Measurements Using the Glucose Sensor", Diabetes Care, vol. 25, No. 6, 2002, pp. 1185-1191.

Monsod, T. P., et al., "Do Sensor Glucose Levels Accurately Predict Plasma Glucose Concentrations During Hypoglycemia and Hyperinsulinemia?" Diabetes Care, vol. 25, No. 5, 2002, pp. 889-893.

Pickup, J., et al., "Implantable Glucose Sensors: Choosing the Appropriate Sensing Strategy", Biosensors, vol. 3, 1987/88, pp. 335-346.

Pickup, J., et al., "In Vivo Molecular Sensing in Diabetes Mellitus: An Implantable Glucose Sensor with Direct Electron Transfer", Diabetologia, vol. 32, 1989, pp. 213-217.

Pishko, M. V., et al., "Amperometric Glucose Microelectrodes Prepared Through Immobilization of Glucose Oxidase in Redox Hydrogels", Analytical Chemistry, vol. 63, No. 20, 1991, pp. 2268-2272.

Quinn, C. P., et al., "Kinetics of Glucose Delivery to Subcutaneous Tissue in Rats Measured with 0.3-mm Amperometric Microsensors", The American Physiological Society, 1995, E155- E161.

Roe, J. N., et al., "Bloodless Glucose Measurements", Critical Review in Therapeutic Drug Carrier Systems, vol. 15, Issue 3, 1998, pp. 199-241.

Sakakida, M., et al., "Development of Ferrocene-Mediated Needle-Type Glucose Sensor as a Measure of True Subcutaneous Tissue Glucose Concentrations", Artificial Organs Today, vol. 2, No. 2, 1992, pp. 145-158.

Sakakida, M., et al., "Ferrocene-Mediated Needle-Type Glucose Sensor Covered with Newly Designed Biocompatible Membrane", Sensors and Actuators B, vol. 13-14, 1993, pp. 319-322.

Salehi, C., et al., "A Telemetry-Instrumentation System for Long-Term Implantable Glucose and Oxygen Sensors", Analytical Letters, vol. 29, No. 13, 1996, pp. 2289-2308.

Schmidtke, D. W., et al., "Measurement and Modeling of the Transient Difference Between Blood and Subcutaneous Glucose Concentrations in the Rat After Injection of Insulin", Proceedings of the National Academy of Sciences, vol. 95, 1998, pp. 294-299.

Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.

Shichiri, M., et al., "Glycaemic Control in Pancreatectomized Dogs with a Wearable Artificial Endocrine Pancreas", *Diabetologia*, vol. 24, 1983, pp. 179-184.

Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.

Shichiri, M., et al., "Membrane Design for Extending the Long-Life of an Implantable Glucose Sensor", *Diabetes Nutrition and Metabolism*, vol. 2, 1989, pp. 309-313.

Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.

Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.

Shichiri, M., et al., "Wearable Artificial Endocrine Pancreas With Needle-Type Glucose Sensor", *The Lancet*, 1982, pp. 1129-1131.

Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.

Sternberg, R., et al., "Study and Development of Multilayer Needle-Type Enzyme-Based Glucose Microsensors", *Biosensors*, vol. 4, 1988, pp. 27-40.

Thompson, M., et al., "In Vivo Probes: Problems and Perspectives", *Clinical Biochemistry*, vol. 19, 1986, pp. 255-261.

Tsalikian, E., et al., "Accuracy of the GlucoWatch G2® Biographer and the Continuous Glucose Monitoring System During Hypoglycemia: Experience of the Diabetes Research in Children Network", *Diabetes Care*, vol. 27, No. 3, 2004, pp. 722-726.

Turner, A., et al., "Diabetes Mellitus: Biosensors for Research and Management", *Biosensors*, vol. 1, 1985, pp. 85-115.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.

Velho, G., et al., "Strategies for Calibrating a Subcutaneous Glucose Sensor", *Biomedica Biochimica Acta*, vol. 48, 1989, pp. 957-964.

Wilson, G. S., et al., "Progress Toward the Development of an Implantable Sensor for Glucose", *Clinical Chemistry*, vol. 38, No. 9, 1992, pp. 1613-1617.

U.S. Appl. No. 11/365,340, Notice of Allowance mailed Nov. 4, 2010.

U.S. Appl. No. 11/365,340, Office Action mailed May 28, 2010.

Cheyne, E. H., et al., "Performance of a Continuous Glucose Monitoring System During Controlled Hypoglycaemia in Healthy Volunteers", *Diabetes Technology & Therapeutics*, vol. 4, No. 5, 2002, pp. 607-613.

Jobst, G., et al., "Thin-Film Microbiosensors for Glucose-Lactate Monitoring", *Analytical Chemistry*, vol. 68, No. 18, 1996, pp. 3173-3179.

Kuure-Kinsey, M., et al., "A Dual-Rate Kalman Filter for Continuous Glucose Monitoring", *Proceedings of the 28th IEEE, EMBS Annual International Conference, New York City*, 2006, pp. 63-66.

Lodwig, V., et al., "Continuous Glucose Monitoring with Glucose Sensors: Calibration and Assessment Criteria", *Diabetes Technology & Therapeutics*, vol. 5, No. 4, 2003, pp. 573-587.

Morbiducci, U, et al., "Improved Usability of the Minimal Model of Insulin Sensitivity Based on an Automated Approach and Genetic Algorithms for Parameter Estimation", *Clinical Science*, vol. 112, 2007, pp. 257-263.

Mougiakakou, et al., "A Real Time Simulation Model of Glucose-Insulin Metabolism for Type 1 Diabetes Patients", *Proceedings of the 2005 IEEE*, 2005, pp. 298-301.

Parker, R., et al., "Robust H∞ Glucose Control in Diabetes Using a Physiological Model", *AIChE Journal*, vol. 46, No. 12, 2000, pp. 2537-2549.

METHOD AND SYSTEM FOR PROVIDING CONTINUOUS CALIBRATION OF IMPLANTABLE ANALYTE SENSORS

RELATED APPLICATION

The present application is a continuation of U.S. patent application Ser. No. 11/365,340 filed Feb. 28, 2006, entitled "Method and System for Providing Continuous Calibration of Implantable Analyte Sensors", the disclosure of which is incorporated herein by reference for all purposes.

BACKGROUND

Continuous monitoring of analytes of a patient generally uses an analyte sensor that that is at least partially implanted in the patient so as to be in fluid contact with the patient's analytes such as interstitial fluid or blood. The analyte sensor typically is replaced after a predetermined time period such as three, five or seven day period, when a new sensor is implanted in the patient to replace the old sensor. During the sensor replacement process, a gap or interruption in the analyte monitoring occurs. For example, during the time period in which the patient removes the implanted analyte sensor to replace with a new analyte sensor, the patient is unable to monitor or determine the analyte values such as glucose levels. In this manner, with continuous glucose monitoring systems presently available which use short term analyte sensors, there is always a gap in service during which data associated with the measurement of the patient's analyte levels cannot be obtained.

In addition, calibration of each implanted analyte sensor, which is necessary before data from the analyte sensor can be obtained, is laborious, time consuming, and error prone. Factory calibration is not a practical approach due to substantial sensor to sensor variability of signal strength introduced during the manufacturing process, and also, due to additional variability imposed by the sensors' response to the in-vivo environment which varies from patient to patient.

Thus, typically it is necessary to perform in-vivo calibration, in which the analyte sensor is calibrated, post implantation, by comparison with a reference blood glucose value. Generally these reference blood glucose values include capillary blood glucose values obtained by finger or arm stick using a conventional blood glucose meter. To perform the calibration using the reference blood glucose values, a substantial number of capillary values such as, for example, one to four capillary measurements daily, are necessary to ensure the continued calibration (and thus, accurate) values determined by the analyte sensors.

Moreover, calibrations may sometimes be inaccurate due to transient sensitivity changes which generally occur early in the lifetime of an implanted sensor, and sometimes referred to as early sensitivity attenuation, or ESA. If a calibration is assigned to an analyte sensor undergoing a transient change in sensitivity, inaccurate sensor readings or measurements will result at a later point in time, when the sensitivity reverts to its "true" value.

Further, the typical calibration process is performed for each newly implanted glucose sensor. More specifically, with the placement of each glucose sensor, a new set of blood capillary reference values are obtained, and which is the sole basis (or reference) for calibration of that particular sensor during the usage life of the sensor, for example, during a three, five or a seven day period.

In view of the foregoing, it would be desirable to have an approach to provide methods and system for continuous analyte monitoring where no gap in service can be achieved. In addition, it would be desirable to have methods and a system to verify the stability of a newly implanted sensor, before obtaining user-accessible analyte data from the sensor. Furthermore, it would be desirable to have methods and system for continuous analyte monitoring for continuous calibration of analyte sensors and which minimizes the number of necessary fingerstick (or armstick) calibrations of the analyte sensors using glucose meters, and also, to provide alternate reference.

SUMMARY OF THE INVENTION

In view of the foregoing, in accordance with the various embodiments of the present invention, there is provided a method and system in which short term sensors may be calibrated based on the data associated with prior short term sensors by providing an overlap in the sensor placement during the sensor replacement process such that fewer, or in the limit, no additional capillary blood glucose values are needed for calibration of subsequent sensors, and further, analyte levels are continuously monitored without any interruption, for example, during the periodic sensor replacements in the continuous analyte monitoring system.

These and other objects, features and advantages of the present invention will become more fully apparent from the following detailed description of the embodiments, the appended claims and the accompanying drawings.

DETAILED DESCRIPTION

Figure 1:
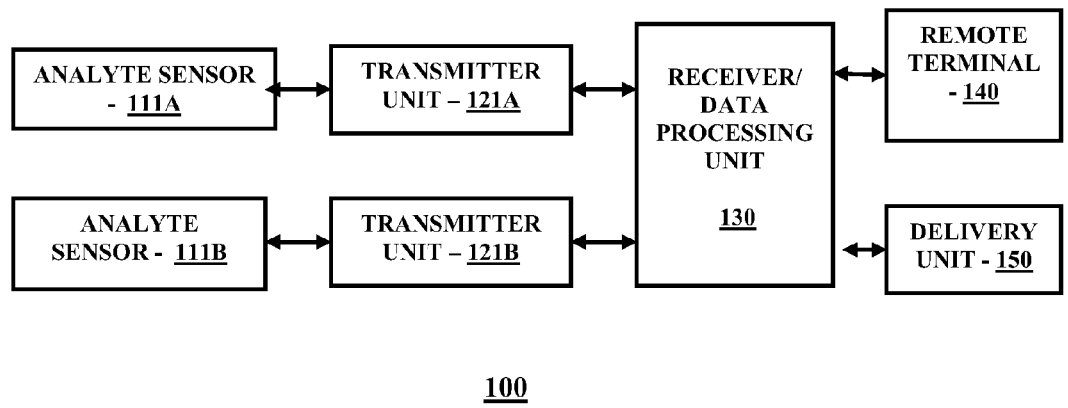
FIG. 1 is a block diagram illustrating a continuous analyte monitoring system for practicing one embodiment of the present invention.

FIG. 1 is a block diagram illustrating a continuous analyte monitoring system for practicing one embodiment of the present invention. Referring to FIG. 1, a continuous analyte monitoring system 100 includes analyte sensor 111A operatively coupled to a transmitter unit 121A, and analyte sensor 111B operatively coupled to transmitter unit 121B. Further shown is a receiver/data receiving unit 130 which is operatively coupled to transmitter unit 121A and transmitter unit 121B. The receiver/data processing unit 130 in one embodiment is configured to communicate with a remote terminal 140 and a delivery unit 150. The remote terminal 140 in one embodiment may include for example, a desktop computer terminal, a data communication enabled kiosk, a laptop computer, a handheld computing device such as a personal digital assistant (PDAs), or a data communication enabled mobile telephone. Moreover, the delivery unit 150 may include in one embodiment, but not limited to, an external infusion device such as an external insulin infusion pump, an implantable pump, a pen-type insulin injector device, a patch pump, an inhalable infusion device for nasal insulin delivery, or any other type of suitable delivery system.

Referring to FIG. 1, the receiver/data receiving unit 130 is configured to receive analyte related data from transmitter unit 121A and transmitter unit 121B over a wireless data communication link such as, but not limited to radio frequency (RF) communication link, Bluetooth® communication link, infrared communication link, or any other type of suitable wireless communication connection between two or more electronic devices which may further be uni-directional (e.g., from transmitter units 121A, 121B to receiver/data processing unit 130), or alternatively, bi-directional between the two or more devices. Alternatively, the data communication link connecting the transmitter units 121A and 121B to the receiver/data processing unit 130 may include wired cable connection such as, for example, but not limited to RS232 connection, USB connection, or serial cable connection.

In an alternate embodiment, each of the transmitters 121A and 121B may be individually coupled to a corresponding receiver section (for example, separate receiver/data processing sections of the receiver/data processing unit 130) such that each transmitter 121A and 121B are uniquely operatively coupled to the respective receiver/data processing units. In addition, each receiver/data processing unit may be configured to communicate with each other such that data from the transmitters 121A and 121B may be interchangeably communicated. Furthermore, while FIG. 1 illustrates a single receiver/data processing unit 130, within the scope of the present invention, multiple discrete receiver/data processing units may be provided, each uniquely configured to communicate with a corresponding one of the transmitter units 121A, 121B.

Furthermore, in yet another embodiment of the present invention, the transmitter unit 121A and transmitter unit 121B may be physically coupled in a single housing so as to provide a single transmitter section for the patient, which is configured to support multiple transmitter units 121A, 121B. Moreover, while two transmitter units 121A, 121B are shown in FIG. 1, within the scope of the present invention, the continuous analyte monitoring system 100 maybe configured to support additional and/or multiple transmitter units, multiple remote terminals, and receiver/data processing units.

Moreover, referring to FIG. 1, the analyte sensors 111A and 111B may include, but are not limited to short term subcutaneous analyte sensors or transdermal analyte sensors, for example, which are configured to detect analyte levels of a patient over a predetermined time period, and after which, a replacement of the sensors is necessary. Moreover, in one embodiment, the transmitter units 121A, 121B are configured to receive analyte related data from the corresponding analyte sensors 111A, 111B, respectively, and to transmit data to the receiver/data processing unit 130 for further processing.

The transmitter units 121A, 121B may, in one embodiment, be configured to transmit the analyte related data substantially in real time to the receiver/data processing unit 130 after receiving it from the corresponding analyte sensors 111A, 111B respectively. For example, the transmitter units 121A, 121B may be configured to transmit once per minute to the receiver/data processing unit 130 based on analyte levels detected by the corresponding analyte sensors 111A, 111B respectively. While once per minute data transmission is described herein, within the scope of the present invention, the transmitter units 121A, 121B may be configured to transmit analyte related data more frequently (such as, for example, once every 30 seconds), or less frequently (for example, once every 3 minutes).

Additional analytes that may be monitored, determined or detected by analyte sensors 111A, 111B include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be determined.

Moreover, within the scope of the present invention, transmitter units 121A, 121B may be configured to directly communicate with one or more of the remote terminal 140 or the delivery unit 150, and in addition, the receiver/data processing unit 130 may be integrated with one or more of the remote terminal 140 or the delivery unit 150. Furthermore, within the scope of the present invention, additional devices may be provided for communication in the continuous analyte monitoring system 100 including additional receiver/data processing unit, remote terminals (such as a physician's terminal) and/or a bedside terminal in a hospital environment, for example.

In accordance with the various embodiments of the present invention, the analyte sensors 111A, 111B may be inserted through the skin of the patient using insertion devices having a predefined or configured insertion mechanism (spring loaded devices, for example) which facilitates the placement and positioning of the analyte sensors through the patient's skin, and so as to be in fluid contact with the patient's analytes. Alternatively, the sensors 111A, 111B may be manually deployed using an insertion guide or needle.

As described in further detail below, the continuous calibration process in one embodiment includes deploying and calibrating a first sensor (e.g., analyte sensor 111A) at predetermined time intervals using finger stick calibrations, for example, at 10 hours, 12 hours, 24 hours and 72 hours from the initial insertion of the first sensor 111A. Moreover, the first and subsequent analyte measurements may be obtained after the initial calibration at 10 hours when the analyte sensor has substantially reached a stability point. Thereafter, prior to the termination of the first sensor life (for example, at the $120^{th}$ hour for a 5 day sensor), a second analyte sensor (for example, sensor 111B) is inserted into the patient and during the period of overlap of the first and second analyte sensors 111A, 111B, the second analyte sensor 111B is correlated with the first analyte sensor 111A values and the second analyte sensor 111B is calibrated in reference to the first analyte sensor 111A values such that the second analyte sensor 111B and any additional subsequent analyte sensors do not require the multiple (or preferably, any) fingerstick calibrations as is the case for the first analyte sensor 111A.

In this manner, the short term analyte sensors are overlapped for a predetermined time period to allow the output of the first and second sensors to be correlated to detect potential transient sensitivity (e.g., ESA) in the second sensor. The detection of potential transient sensitivity in the second sensor can be achieved with substantial accuracy since the first sensor has had a substantial time period (e.g., several days of usage) to stabilize. Upon establishing an acceptable level of correlation, the calibration of the first sensor in one embodiment is assigned or transferred to the second sensor. More specifically, in one embodiment, the continuous data from a previously calibrated first sensor is used as a set of reference values to calibrate the second newly implanted sensor.

In this manner, in one embodiment of the present invention, a substantially accurate calibration may be assigned to the second sensor while using no additional capillary blood glucose values for calibration, and further, this approach of correlation and transfer calibration may be repeated for subsequent sensors in the continuous monitoring system 100 such that analyte levels are continuously monitored without any interruption, for example, during the periodic sensor replacements in the continuous analyte monitoring system 100.

Figure 2:
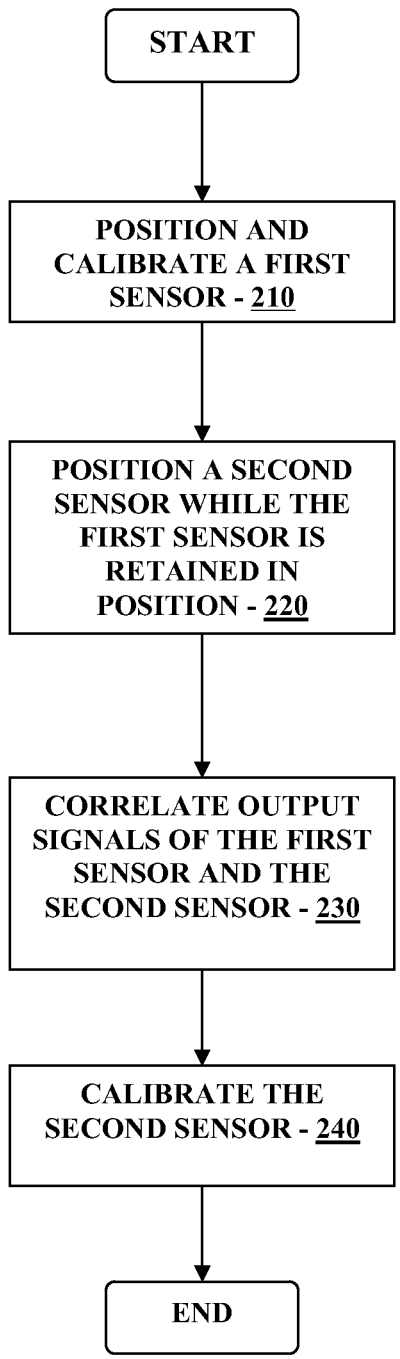
FIG. 2 is a flowchart illustrating the continuous calibration of analyte sensors in the continuous analyte monitoring system in accordance with one embodiment of the present invention.

FIG. 2 is a flowchart illustrating the continuous calibration of analyte sensors in the continuous analyte monitoring system in accordance with one embodiment of the present invention. Referring to FIG. 2, at step 210 a first sensor 111A (FIG. 1) is deployed through the patient's skin so as to be in fluid contact with the patient's analyte and periodically calibrated at, for example, $10^{th}$ hour, $12^{th}$ hour, $24^{th}$ hour, and $72^{nd}$ hour. Data associated with the detected or monitored analyte level from the first sensor 111A may be obtained for further analysis such as insulin therapy and treatment on or after the $10^{th}$ hour calibration when the first sensor has substantially reached an acceptable stabilization level.

More specifically, the transmitter unit 121A (FIG. 1) is configured in one embodiment to continuously transmit the data received from the analyte sensor 111A to the receiver/data processing unit 130 (FIG. 1). The receiver/data processing unit 130 may be configured in one embodiment, to display the received, substantially real time values corresponding to the patient's monitored analyte levels graphically, audibly, and or a combination of visual and audio output including graphs, trend arrows, and level indicators associated with different sound levels or ringtones based on the analyte levels.

Referring to FIG. 2, at step 220, a second analyte sensor 111B is positioned at a predetermined time prior to the scheduled removal of the first analyte sensor 111A. In one embodiment, the predetermined time overlap between the insertion of the second analyte sensor 111B and the removal of the first analyte sensor 111A from the patient may be a two to ten hour period. Alternatively, the time overlap may be longer or shorter depending upon the sensor configuration and the preceding time periods are provided as examples for illustrative purposes only. In one embodiment, the time overlap may be variable, such that first analyte sensor 111A is removed when second analyte sensor 111B is determined to have reached a point of stable operation. Thereafter, at step 230, the output data or signals from the first sensor 111A received from transmitter unit 121A is correlated with the output data or signals from the second sensor 111B received from the transmitter unit 121B. That is, the receiver/data processing unit 130 (FIG. 1) in one embodiment is configured to receive the simultaneous or substantially near simultaneous data transmission from a plurality of transmitter units in the continuous analyte monitoring system 100. More specifically, in one embodiment, the receiver/data processing unit 130 may be configured to correlate the data from the two sensors 111A, 111B so as to, for example, determine that the correlation of the two data sets are sufficiently robust to determine the stability and thus acceptability of the second sensor 111B.

Referring again to FIG. 2, after correlating the data of the two sensors 111A, 111B, at step 240, the second sensor is calibrated based on one or more scaling factors associated with the two sensors 111A, 111B, from which the sensitivity of the second sensor 111B may be determined. Thereafter, when the second sensor 111B is calibrated, the first sensor 111A may be removed from the patient, and the data or signals associated with the patient's analyte levels from the second sensor 111B may be used by the patient for further analysis and/or treatment.

In the manner described above, in one embodiment of the present invention, there is provided a system and method of continuously calibrating implanted analyte sensors that provide accurate detection of initial instabilities of the implanted sensors, reduce the number of required blood capillary tests for calibration, increase the calibration accuracy, and also, eliminate any gaps or interruptions in the continuous analyte data or record monitored by the continuous monitoring system 100.

Moreover, in a further embodiment, the receiver/data processing unit 130 may be configured to prompt the patient for confirmation and also, for the sensor calibration code when the receiver/data processing unit 130 detects data or signals received from the transmitter unit 121B coupled to the second sensor 111B.

Figure 3:
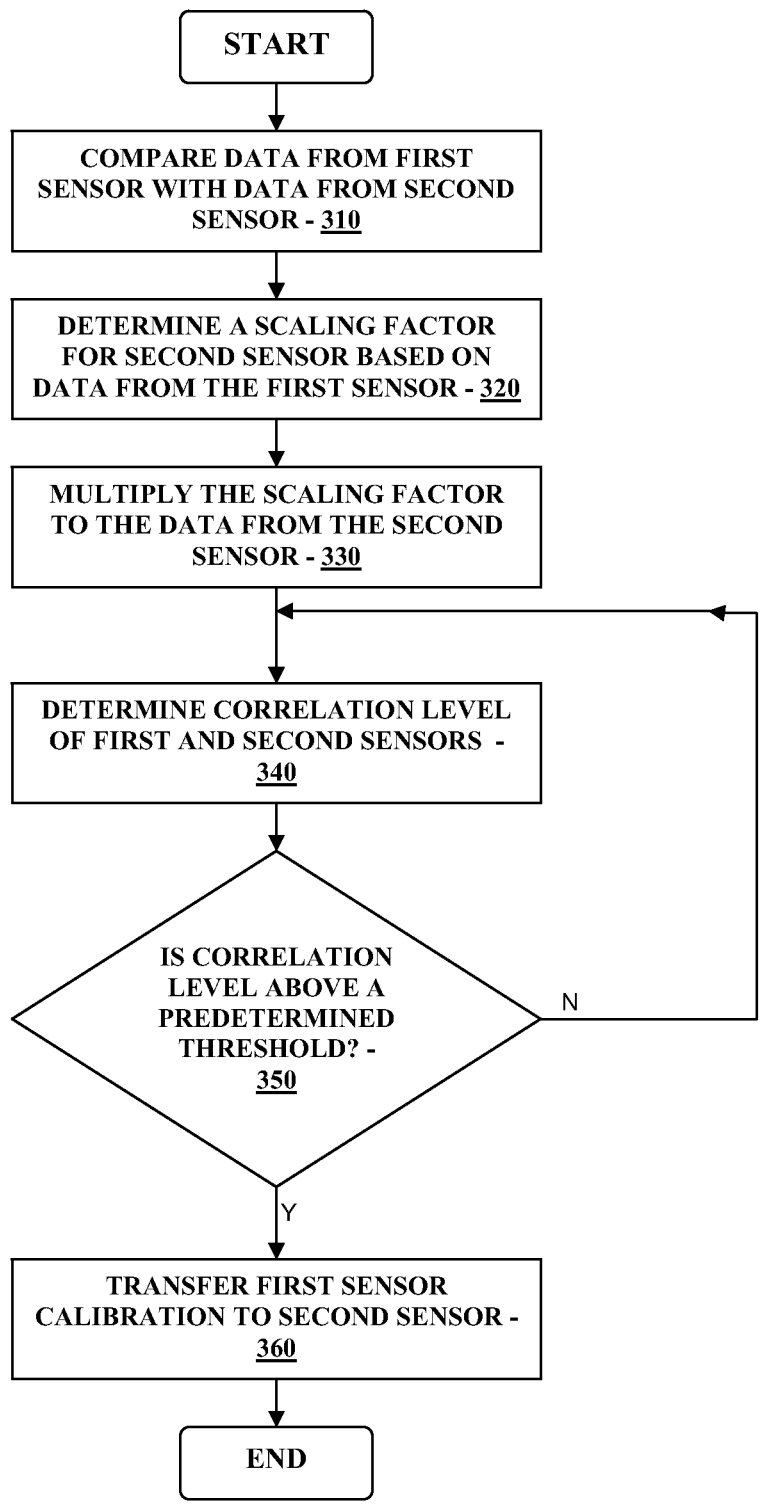
FIG. 3 is a flowchart illustrating correlation and calibration steps 230, 240 of the continuous calibration of analyte sensors in the continuous analyte monitoring system shown in FIG. 2 in accordance with one embodiment of the present invention.

FIG. 3 is a flowchart illustrating correlation step 230 and calibration step 240 of the continuous calibration of analyte sensors in the continuous analyte monitoring system shown in FIG. 2 in accordance with one embodiment of the present invention. Referring to FIG. 3, at step 310, the receiver/data processing unit 130 (FIG. 1) is configured to compare the analyte associated data or signals from the transmitter unit 121A corresponding to analyte levels detected by the first sensor 111A with the analyte associated data or signals from the transmitter unit 121B corresponding to analyte levels detected by the second sensor 111B at each time period of the analyte monitoring.

Thereafter, at step 320, the receiver/data processing unit 130 is configured to determine a scaling factor for the second sensor 111B based on the data or signals from the first sensor 111A. More specifically, in one embodiment, the receiver/data processing unit 130 is configured to perform a predefined autocorrelation function to determine the scaling factor for the second sensor 111B. Alternatively, in another embodiment, the data from the second sensor 111B is multiplied by a range of predetermined initial scaling factors to determine an average error between the data from the first sensor 111A and the data from the second sensor 111B. Based on the calculated average error, the scaling factor is determined as the one of the predetermined initial scaling factors which yield the smallest possible calculated average error.

In a further embodiment, the scaling factor may be determined by calculating an average of the ratio of the two raw signals from the first sensor 111A and the second sensor 111B, or any other suitable manner in which to determine a suitable scaling factor.

Referring to FIG. 3, after the scaling factor is determined at step 320, the scaling factor is applied to the data from the second sensor 111B at step 330. More specifically, in one embodiment, the determined scaling factor at step 320 is multiplied to the data from the second sensor 111B at step 330. Thereafter, at step 340, a correlation level of the first and second sensors 111A, 111B respectively, is determined by the receiver/data processing unit 130 (FIG. 1). More specifically, at step 340, the level of correlation of data from the first sensor 111A and the second sensor 111B are determined as a function of a predetermined limit, where, in the case where the level of correlation is too small such that the minimum average error is too large, then it is determined that the second sensor 111B is unstable.

In other words, referring back to FIG. 3, at step 340, the correlation level is determined and at step 350, it is determined whether the correlation level is above a predetermined threshold. As shown in the Figure, if it is determined at step 350 that the correlation level is not above the predetermined threshold level, then the receiver/data processing unit 130 returns the routine to step 340 to determine again the correlation level of the first sensor 111A and the second sensor 111B. If at step 350 it is determined that the correlation level is above the predetermined threshold level, then the receiver/data processing unit 130 determines that the second sensor 111B is relatively stable, and at step 360, the first sensor 111A calibration is transferred to the second sensor 111B.

In other words, once it is determined that the second sensor 111B is stable, then a sensitivity may be determined for the second sensor 111B based on the scaling factor determined at step 320 and the sensitivity of the first sensor 111A. This determination may be expressed as follows:

$$S_2 = S_1 * \Sigma(I_2/I_1) \quad (1)$$

where $S_2$ represents the sensitivity of the second sensor 111B, $S_1$ represents the sensitivity of the first sensor 111A, and $\Sigma(I_2/I_1)$ represents the scaling factor which correlates the data of the first sensor 111A and the second sensor 111B.

In this manner, once the second sensor 111B is calibrated, the accuracy of data from the second sensor 111B is substantially similar to the accuracy of the data from the first sensor 111A, where the calibration of the second sensor 111B was performed without any capillary blood glucose measurements by, for example, fingerstick testing using glucose meters. By way of an example, based on a first sensor sensitivity $S_1$ at 0.686 nA/mM, and with a scaling factor $\Sigma(I_2/I_1)$ of 0.725, the sensitivity $S_2$ of the second sensor 111B is determined to be 0.497 nA/mM.

In the manner described above, in one embodiment of the present invention, there is provided a system and method of continuously calibrating implanted analyte sensors that provide accurate detection of initial instabilities of the implanted sensors, reduce the number of required blood capillary tests for calibration, increase the calibration accuracy, and also, eliminate any gaps or interruptions in the continuous analyte data or record monitored by the continuous monitoring system 100.

Moreover, in accordance with the present invention, using the data correlation during the time period when the sensors overlap in time, the calibration frequency may be reduced while increasing the calibration accuracy. Moreover, additional calibration information may also be obtained from the sensor calibration codes predetermined and assigned during sensor manufacturing, and which may be used to improve calibration accuracy without requiring additional or increased capillary blood glucose testing.

Figure 4:
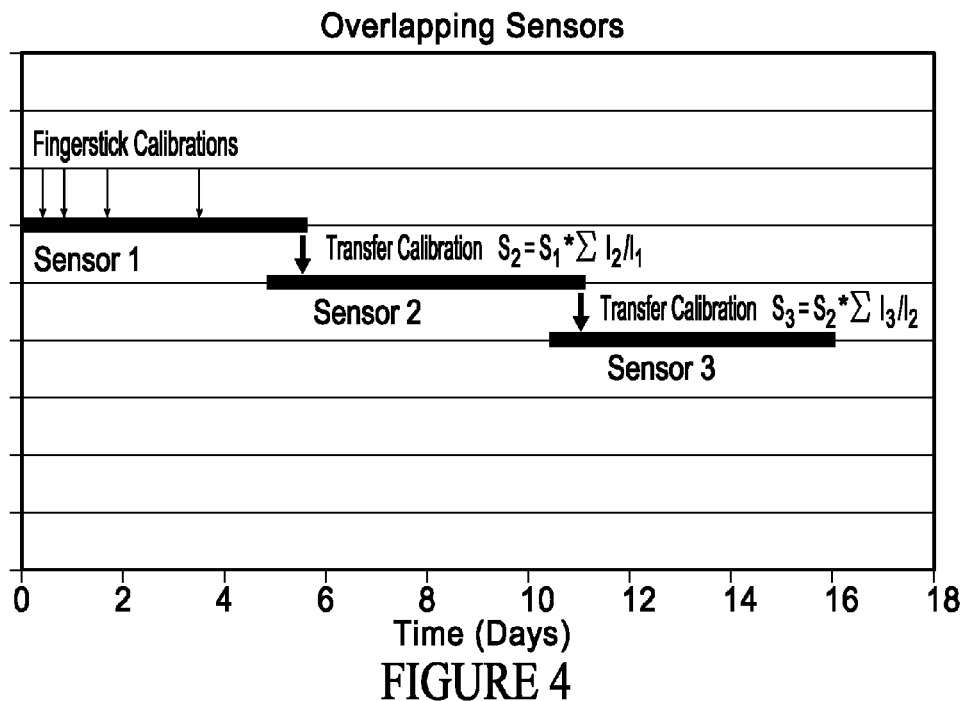
FIG. 4 is a chart illustrating the timing of the continuous calibration of analyte sensors in the continuous analyte monitoring system in accordance with one embodiment of the present invention.

FIG. 4 is a chart illustrating the timing of the continuous calibration of analyte sensors in the continuous analyte monitoring system in accordance with one embodiment of the present invention. Referring to the Figure, each sensor is configured to be approximately a 5-day sensor, with only the first sensor (sensor 1) provided with four discrete fingerstick calibrations using capillary blood glucose measurements. It can be further seen that each sensor overlaps in time such that a predetermined time period overlaps after the insertion and positioning of a subsequent sensor, and before to the removal of the prior sensor. Moreover, calibration of sensor 2 and sensor 3 (and additional sensors thereafter) are performed based on the continuous calibration approach described above using the data correlation and transfer calibration as described.

Figure 5:
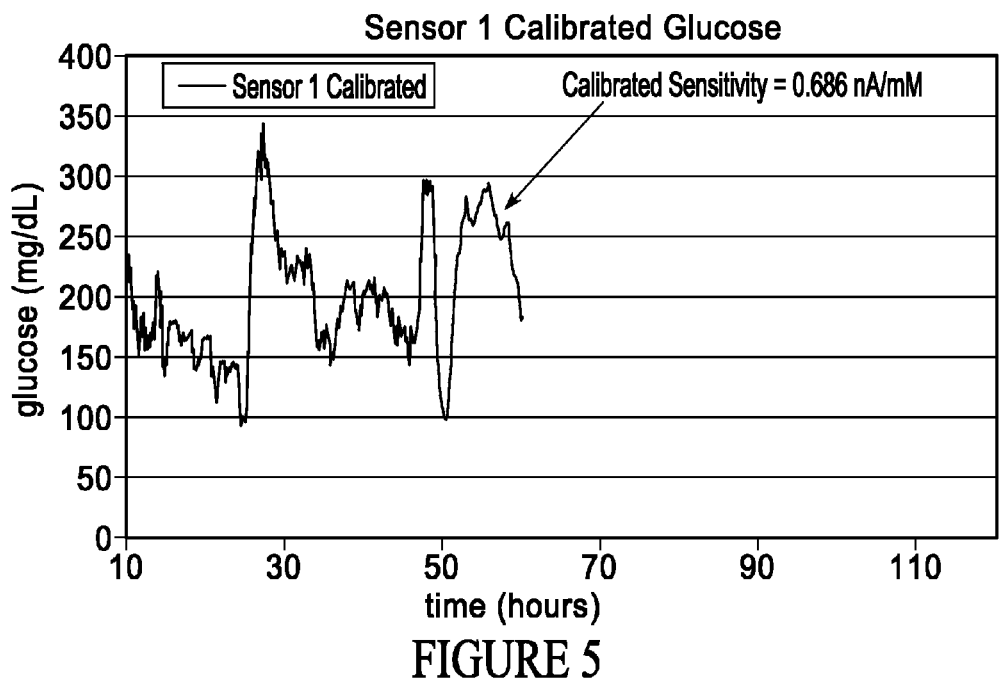
FIG. 5 is a chart illustrating the measured analyte values of a first calibrated analyte sensor in the continuous analyte monitoring system in accordance with one embodiment of the present invention.

FIG. 5 is a chart illustrating the measured analyte values of a first calibrated analyte sensor in the continuous analyte monitoring system in accordance with one embodiment of the present invention. Referring to FIG. 5, it can be seen that over the initial 60 or so hours of glucose level measurements, and based on the fingerstick calibration, the calibrated sensitivity $S_i$ of the first sensor may be determined (for example, at 0.686 nA/mM). Thereafter, as described above, the sensitivity of the second and subsequent sensors may be determined based on the first sensor sensitivity $S_1$ and the optimal scaling factor.

Figure 6:
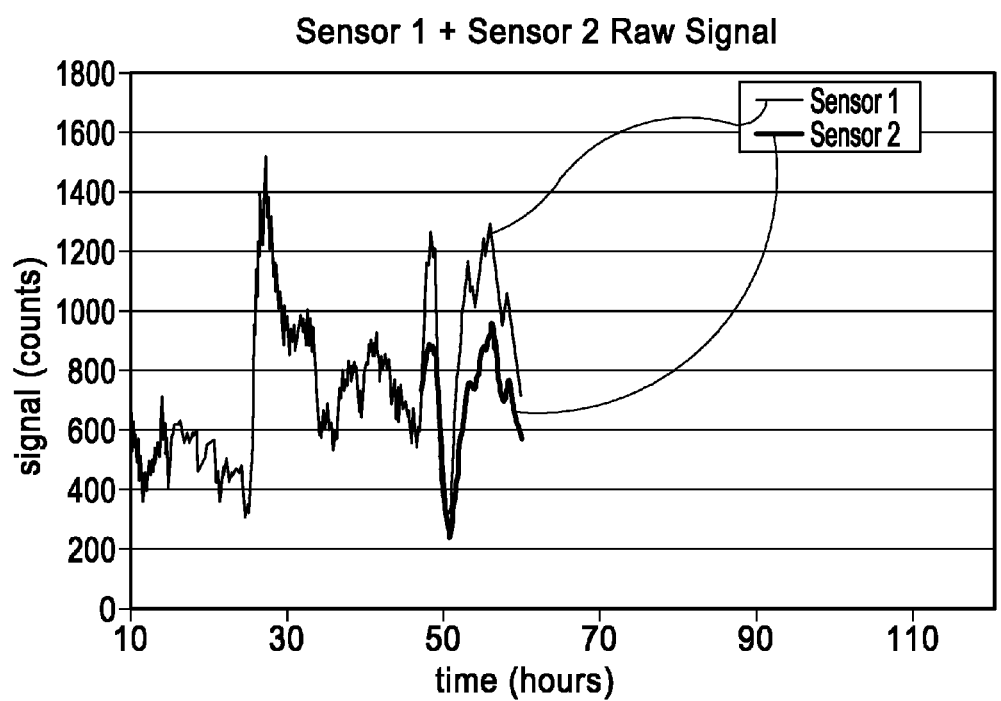
FIG. 6 is a chart illustrating the measured analyte values of a second analyte sensor which is implanted while the calibrated first analyte sensor is implanted in the continuous analyte monitoring system in accordance with one embodiment of the present invention.

FIG. 6 is a chart illustrating the measured analyte values of a second analyte sensor which is implanted while the calibrated first analyte sensor is implanted in the continuous analyte monitoring system in accordance with one embodiment of the present invention. More specifically, FIG. 6 illustrates, in an overlay manner, the calibrated signals from the first sensor 111A and uncalibrated signals from the second sensor 111B received by the receiver/data processing unit 130 over the time period during which the first sensor 111A is retained in inserted position, and while the second sensor 111B is introduced in the patient. It should be noted that the signal count as shown on the Y-axis may be converted to a current signal level by a multiplication factor of 11.5 pico-amps/count.

Figure 7:
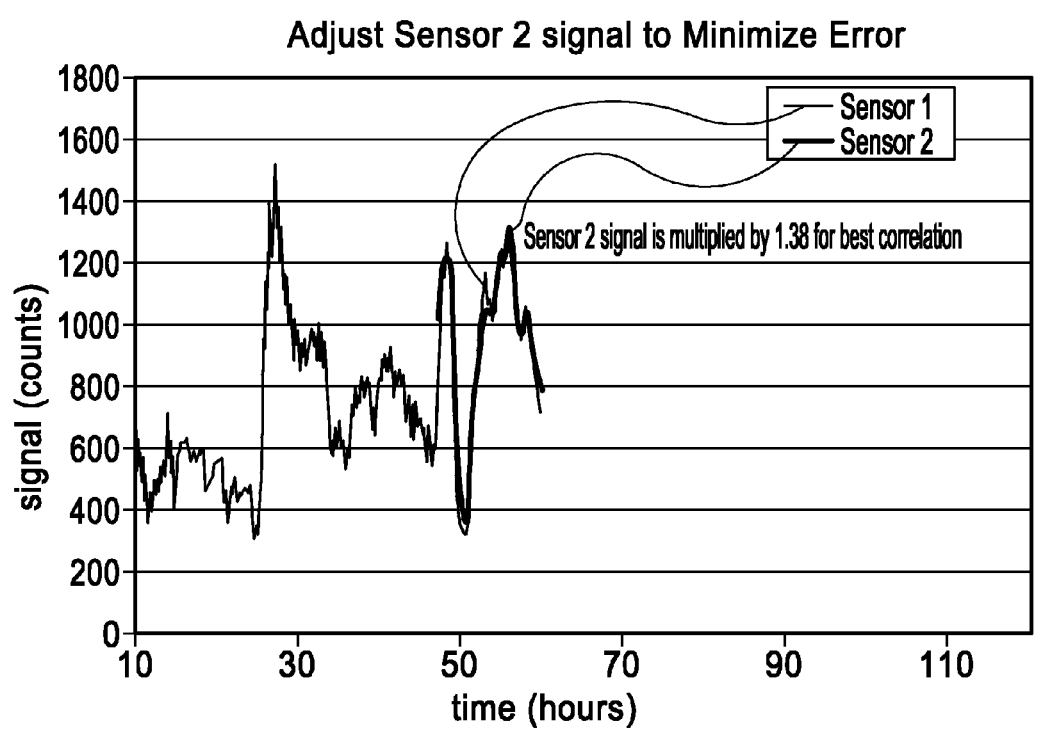
FIG. 7 is a chart illustrating the measured analyte values of the second analyte sensor which is calibrated and correlated with the measured values from the calibrated analyte sensor in accordance with one embodiment of the present invention.

FIG. 7 is a chart illustrating the measured analyte values of the second analyte sensor which is calibrated and correlated with the measured values from the calibrated analyte sensor in accordance with one embodiment of the present invention. More specifically, as can be seen from FIG. 7, in the scaling factor and the correlation of the data from the second sensor 111B with the calibrated data from the first sensor 111A substantially aligns the two data sets over the overlap time period, effectively, providing calibration to the raw data from the second sensor 111B based on the calibrated data from the first sensor 111A.

Figure 8:
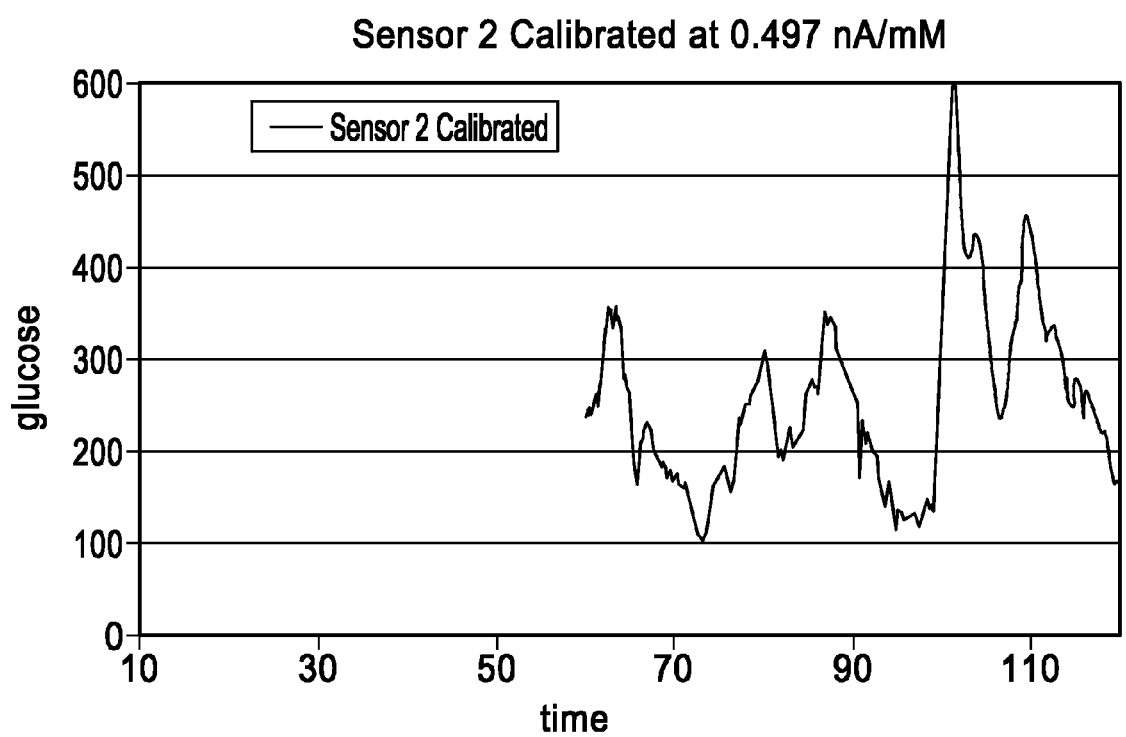
FIG. 8 is a chart illustrating measured analyte values after the removal of the first analyte sensor, and from the calibrated second analyte sensor in accordance with one embodiment of the present invention.

FIG. 8 is a chart illustrating measured analyte values after the removal of the first analyte sensor, and from the calibrated second analyte sensor in accordance with one embodiment of the present invention. In FIG. 8, it can be seen that the first sensor 111A is removed from the patient and thus the receiver/data processing unit 130 (FIG. 1) no longer receives data from the transmitter unit 121A coupled to the sensor 111A. On the other hand, the second sensor 111B is now calibrated and the data received from the second sensor 111B is received by the receiver/data processing unit 130. In this manner, it can be seen that there is no interruption in the measured analyte levels even during the transition state where the short term sensors are replaced.

Accordingly, a method of providing continuous calibration of analyte sensors in one embodiment of the present invention includes calibrating a first sensor, receiving data associated with detected analyte levels from the first sensor, and calibrating a second sensor with reference to one or more detected analyte levels from the first sensor.

The method in one embodiment may further include a step of calibrating a third sensor based on a second scaling factor and data associated with detected analyte levels from the second sensor. Moreover, the step of calibrating the second sensor may in one embodiment, start after a predetermined time period has passed where the first sensor has been in fluid contact with an analyte of a patient, where the predetermined time period may include at least approximately 90% or alternatively, 50% of the life of the first sensor.

In yet another embodiment, the method may further include the step of determining a sensitivity of the first sensor.

In another aspect, the method may also include the step of receiving data associated with detected analyte levels from the second sensor.

In accordance with still another embodiment, the step of calibrating the second sensor may include the steps of determining an analyte level, and comparing the determined analyte level with the data associated with the detected analyte level from the first sensor.

The step of calibrating the second sensor in yet another embodiment may include the steps of determining a scaling factor based on substantially simultaneous data from the first sensor and the second sensor, applying the scaling factor to the data from the second sensor, determining a correlation level of data from the first sensor and from the second sensor.

In another aspect, the step of determining the scaling factor may include the steps of comparing the substantially simultaneous data from the first sensor with the data from the second sensor, and determining the scaling factor based on a calculated scaling factor with the lowest level of average error between the data of the first sensor and the data of the second sensor.

The method in yet another embodiment may include the step of comparing the correlation level with a predetermined correlation threshold defining an acceptable stability level of the second sensor.

The first sensor and the second sensor may be analyte sensors.

This may further include the step of removing the first sensor while retaining the second sensor in fluid contact with the analyte of a patient.

In addition, the first sensor and the second sensor may be subcutaneously positioned under a skin of a patient, where at least a portion of the first sensor and at least a portion of the second sensor are in fluid contact with the patient's analyte.

A system for providing continuous analyte sensor calibration in accordance with another embodiment of the present invention includes a first sensor for subcutaneous placement in a patient, a second sensor for subcutaneous placement in the patient after calibration of the first sensor, where at least a portion of the first sensor and at least a portion of the second sensor are in fluid contact with the patient's analyte substantially simultaneously for a time period.

In one aspect, the time period may be predetermined and includes approximately 2 hours to 10 hours.

Alternatively, in another aspect, the time period may be variable, and where the variable time period may be determined to be when the analyte levels measured by the first and second sensors are within a correlation range, the correlation range being determined by a preset threshold value.

The second sensor may subcutaneously placed in the patient after a predetermined time period has passed where the first sensor has been in fluid contact with an analyte of a patient, and where the predetermined time period includes at least approximately 90% or 50% of the life of the first sensor.

In a further embodiment, the first sensor may be operatively coupled to a first transmitter unit, and the second sensor is operatively coupled to a second transmitter unit, the first and second transmitter units configured to receive data from the corresponding first and second sensors, respectively, for transmission over a communication link.

The first transmitter unit and the second transmitter unit may be coupled to a single transmitter housing.

The communication link may include one or more of an RF communication link, a Bluetooth® communication link, an infrared communication link, or a cable communication link.

The system in another embodiment may include a receiver unit configured to substantially simultaneously receive data from the first transmitter unit and the second transmitter unit.

The receiver unit may include a first receiver section operatively coupled to the first transmitter unit, and a second receiver section operatively coupled to the second transmitter unit, the second receiver section further operatively coupled to the first receiver section for data communication.

The receiver unit may also include an infusion device.

The receiver unit may be configured to calibrate the second sensor based on analyte levels measured by the first sensor.

The receiver unit may be configured to receive data from one or more of the first sensor or the second sensor at predetermined time intervals such that there is no interruption in the received data after the first sensor is removed from the patient.

A method in another embodiment of the present invention may include positioning a first sensor in fluid contact with an analyte of a patient, calibrating the first sensor, positioning a second sensor in fluid contact with the analyte of the patient after calibrating the first sensor, calibrating the second sensor based on data from the first sensor, and removing the first sensor while retaining the second sensor in fluid contact.

The second sensor in one embodiment may be subcutaneously placed in the patient after a predetermined time period has passed where the first sensor has been in fluid contact with an analyte of a patient.

In one embodiment, the stability of the second sensor may be verified by correlation of its output with the output of the stabilized first sensor, prior to calibration of the second sensor based on data from the first sensor, and thereafter removing the first sensor while retaining the second sensor in fluid contact.

A system for determining the stability of an analyte sensor calibration in accordance with still yet another embodiment includes a first sensor for subcutaneous placement in a patient, and a second sensor for subcutaneous placement in the patient after calibration of the first sensor, where at least a portion of the first sensor and at least a portion of the second sensor are in fluid contact with the patient's analyte substantially simultaneously for a time period, and further, where the stability of the second sensor is determined with reference to data from the first sensor.

The time period may be predetermined and includes approximately 2 hours to 10 hours.

Alternatively, the time period may be variable, and where the variable time period may be determined to be when the analyte levels measured by the first and second sensors are within a correlation range which may be determined by a preset threshold value.

A system for determining analyte concentrations in yet another embodiment includes a plurality of analyte sensors, a plurality of transmitter units, each of the plurality of transmitter units operatively coupled to a respective one of the plurality of analyte sensors, a single receiver unit configured to receive and process data substantially simultaneously from all of the plurality of transmitter units, where each transmitter is uniquely couple to a single analyte sensor.

The receiver unit may also include a comparison unit for comparing the one or more signals from the plurality of transmitters units, and also for determining the stability of the plurality of sensors. In addition, the receiver unit may be further configured to determine the calibration of the plurality of sensors based on the comparison unit.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. A system for providing analyte sensor calibration, comprising:
a first analyte sensor configured for fluid contact with an analyte under a skin layer to monitor an analyte level;
a second analyte sensor configured for fluid contact with the analyte under the skin layer to monitor the analyte level; and
one or more processors in signal communication with the first analyte sensor and the second analyte sensor, the one or more processors configured to receive data associated with the monitored analyte level from the first analyte sensor, and to calibrate the second analyte sensor with reference to the received data associated with the monitored analyte level received from the first analyte sensor by determining a scaling factor that includes comparing data from the first analyte sensor with the data from the second analyte sensor and based on an initial scaling factor with a predetermined level of average error between the data of the first analyte sensor and the data of the second analyte sensor, applying the determined scaling factor to the data from the second analyte sensor, and determining a correlation level of signals from the first analyte sensor and the signals from the second analyte sensor.

2. The system of claim 1 further including a third analyte sensor in signal communication with the one or more processors, wherein the one or more processors are configured to calibrate the third analyte sensor based on a second scaling factor and data associated with detected analyte levels from the second analyte sensor.

3. The system of claim 1 wherein the one or more processors are configured to start the calibration of the second analyte sensor after a predetermined time period has elapsed since the first analyte sensor is maintained in fluid contact with the analyte under the skin layer.

4. The system of claim 3 wherein the predetermined time period includes at least approximately 90% of the life of the first analyte sensor.

5. The system of claim 3 wherein the predetermined time period includes at least approximately 50% of the life of the first analyte sensor.

6. The system of claim 1 wherein the one or more processors are configured to determine a sensitivity associated with the first analyte sensor.

7. The system of claim 1 wherein the one or more processors are configured to receive data associated with detected analyte levels from the second analyte sensor.

8. The system of claim 1 wherein the one or more processors are configured to calibrate the second analyte sensor by determining an analyte level and comparing the determined analyte level with the data associated with the detected analyte level from the first analyte sensor.

9. The system of claim 1 wherein the one or more processors are configured to compare the correlation level with a predetermined correlation threshold.

10. The system of claim 9 wherein the predetermined correlation threshold defines an acceptable stability level of the second analyte sensor, and further, when the correlation level is above the predetermined correlation threshold, the one or more processors are configured to determine that the second analyte sensor is stable.

11. The system of claim 10 wherein when the correlation level is above the predetermined correlation level, the one or more processors are configured to calibrate the second analyte sensor with reference to one or more detected analyte levels from the first analyte sensor by transferring one or more calibration parameters associated with calibration of the first analyte sensor to the calibration of the second analyte sensor.

12. The system of claim 9 wherein when the correlation level is above the predetermined correlation level, the one or more processors are configured to calibrate the second analyte sensor with reference to one or more detected analyte levels from the first analyte sensor by transferring one or more calibration parameters associated with calibration of the first analyte sensor to the calibration of the second analyte sensor.

13. The system of claim 9 wherein when the correlation level is below the predetermined correlation threshold, the one or more processors are configured to re-determine the correlation level of the signals from the first analyte sensor and the signals from the second analyte sensor.

14. The system of claim 1 wherein the one or more processors are configured to determine the scaling factor based on an average of the ratio of the signals from the first analyte sensor and the second analyte sensor.

15. The system of claim 1 wherein one or more of the first analyte sensor and the second analyte sensor are glucose sensors.

16. The system of claim 1 wherein the predetermined level of average error between the data of the first analyte sensor and the second analyte sensor includes a lowest level of average error.

17. The system of claim 1 further including an output unit operatively coupled 125 to the one or more processors and configured to output information associated with the monitored analyte level by one or more of the first analyte sensor and the second analyte sensor.

18. The system of claim 1 wherein the one or more processors are configured to calibrate the first analyte sensor based on a reference measurement.

19. The system of claim 1 wherein the one or more processors are configured to calibrate the second analyte sensor in real time when the second analyte sensor is positioned in fluid contact with the analyte under the skin layer.

* * * * *